(12) United States Patent
Trouet et al.

(10) Patent No.: US 7,951,772 B2
(45) Date of Patent: *May 31, 2011

(54) TUMOR-ACTIVATED PRODRUG COMPOUNDS AND TREATMENT

(75) Inventors: Andre Trouet, Herentals (BE); Roger Baurain, Hamme-Mille (BE)

(73) Assignees: La Region Wallonne, Brussels (BE); Universite Catholique de Louvain, Louvain-La-Neuve (BE)

( * ) Notice: Subject to any disclaimer, the term of this patent is extended or adjusted under 35 U.S.C. 154(b) by 202 days.

This patent is subject to a terminal disclaimer.

(21) Appl. No.: 12/157,363

(22) Filed: Jun. 10, 2008

(65) Prior Publication Data

US 2009/0137494 A1    May 28, 2009

Related U.S. Application Data

(60) Division of application No. 11/370,290, filed on Mar. 8, 2006, now Pat. No. 7,390,629, which is a division of application No. 10/012,576, filed on Nov. 9, 2001, now Pat. No. 7,037,898, which is a continuation of application No. 09/298,330, filed on Apr. 23, 1999, now Pat. No. 6,342,480, which is a continuation of application No. 08/793,910, filed as application No. PCT/BE95/00076 on Aug. 21, 1995, now Pat. No. 5,962,216.

(30) Foreign Application Priority Data

Aug. 19, 1994 (BE) .................................. 9400751
Aug. 19, 1994 (BE) .................................. 9400752

(51) Int. Cl.
*A61K 38/00* (2006.01)
(52) U.S. Cl. ...................................... 514/1.3
(58) Field of Classification Search .................. None
See application file for complete search history.

(56) References Cited

U.S. PATENT DOCUMENTS

| | | | |
|---|---|---|---|
| 4,277,466 A | 7/1981 | Trouet et al. |
| 4,296,105 A | 10/1981 | Baurain et al. |
| 4,376,765 A | 3/1983 | Trouet et al. |
| 4,388,305 A | 6/1983 | Trouet et al. |
| 4,636,456 A | 1/1987 | Takahashi et al. |
| 4,671,958 A | 6/1987 | Rodwell et al. |
| 4,703,107 A | 10/1987 | Monsigny et al. |
| 4,719,312 A | 1/1988 | Firestone |
| 4,870,162 A | 9/1989 | Trouet et al. |
| 5,024,835 A | 6/1991 | Rao et al. |
| 5,220,001 A | 6/1993 | Ok et al. |
| 5,599,686 A | 2/1997 | DeFeo-Jones et al. |
| 5,618,790 A | 4/1997 | Kennedy et al. |
| 5,962,216 A | 10/1999 | Trouet et al. |
| 6,143,864 A | 11/2000 | DeFeo-Jones et al. |
| 6,342,480 B1 | 1/2002 | Trouet et al. |
| 7,037,898 B2 | 5/2006 | Trouet et al. |
| 7,390,629 B2 | 6/2008 | Trouet et al. |

FOREIGN PATENT DOCUMENTS

| | | |
|---|---|---|
| BE | 869485 | 12/1978 |
| BE | 882541 | 7/1980 |
| DE | 3841764 | 6/1990 |
| EP | 0041935 A1 | 12/1981 |
| EP | 0044090 A2 | 1/1982 |
| EP | 0126685 A1 | 11/1984 |
| EP | 0208615 B1 | 1/1987 |
| EP | 0126344 A2 | 11/1994 |
| GB | 2027024 | 2/1980 |
| JP | 1-151599 | 6/1989 |
| WO | 81/01145 A1 | 4/1981 |
| WO | 91/15598 A1 | 10/1991 |
| WO | 93/02703 A1 | 2/1993 |
| WO | 94/07518 A1 | 4/1994 |
| WO | 94/15909 A1 | 7/1994 |
| WO | 96/00503 A1 | 1/1996 |
| WO | 96/33198 A1 | 10/1996 |
| WO | 00/69472 A2 | 11/2000 |
| WO | 01/28593 A2 | 4/2001 |
| WO | 01/30804 A2 | 5/2001 |

OTHER PUBLICATIONS

Balajthy et al., "Synthesis and Functional Evaluation of a Peptide Derivative of 1-b-D-Arabinofuranosylcytosine," J. Med. Chem., vol. 35:3344-3349 (1992).
Baurain et al., "Amino Acid and Dipeptide Derivatives of Daonorubicin. 2. Cellular Pharmacology and Antitumor Activity on L1210 Leukemic Cells in Vitro and in Vivo," J. Med. Chem., vol. 23:1171-1174 (1980).
Baurain et al., "Antitumor Activity of Daunorubicin Linked to Proteins: Lysosomal Hydrolysis and Antitumor Activity of Conjugates Prepared with Peptidic Spacer Arms," Chem. Abstr., #97:150636, 1982.
Baurain et al., "Targeting of Daunorubicin by Covalent and Reversible Linkage to Carrier Proteins. Lysosomal Hydrolysis and Antitumoral Activity of Conjugates Prepared with Peptidic Spacers," Drugs Exp. Clin., vol. 9:303-311 (1983).
Carl, P.L., et al. "Protease-activated "prodrugs" for cancer chemotherapy." Proc Nati Acad Sci USA. Apr. 1980; 77 (4):2224-8.
Chakravarty et al., "Plasmin-Activated Prodrugs for Cancer Chemotherapy. 1. Synthesis and Biological Activity of Peptidylacivicin and Peptidylphenylenediamine," J. Med. Chem., vol. 26:633-638 (1983).
Chakravarty et al., "Plasmin-Activated Prodrugs for Cancer Chemotherapy. 2. Synthesis and Biological Activity of Peptidyl Derivatives of Doxorubicin," J. Med. Chem., vol. 26:638-644 (1983).

(Continued)

*Primary Examiner* — Andrew D Kosar
(74) *Attorney, Agent, or Firm* — Nelson Mullins Riley & Scarborough LLP; Jane E. Remillard, Esq.; Pankaj N. Desai

(57) ABSTRACT

The compound (W-Z-M) according to the invention comprises a component (M) chosen from the group consisting of markers and therapeutic agents possessing an intracellular active site (A.S.), linked to a ligand (W-Z) comprising an arm (Z) linked to a terminal group (W), characterized in that the linkage between the arm (Z) of the ligand (W-Z) and the component (M) prevents intracellular entry of the compound (W-Z-M) and/or inhibits expression of the marker (M), in that said linkage can be selectively cleaved by factors secreted by target cells so as to permit expression of the marker (M) or entry of the therapeutic agent (M) into said target cells, and in that the terminal group (W) provides for the stability of the compound (W-Z-M) in the serum and circulating blood.

14 Claims, 19 Drawing Sheets

OTHER PUBLICATIONS

Cruciani, Ricardo A. et al., "Antibiotic magainins exert cytolytic activity against transformed cell lines through channel formation," Proc. Natl. Acad. Sci. USA, vol. 88:3792-3796 (1991).
DeFeo-Jones, D., et al. "A peptide-doxorubicin 'prodrug' activated by prostate-specific antigen selectively kills prostate tumor cells positive for prostate-specific antigen in vivo." Nat Med. Nov. 2000; 6(11):1248-52.
De Marre et al., "Evaluation of the Hydrolytic and Enzymatic Stability of Macromolecular Mitomycin C Derivatives," J. Controlled Release, vol. 31:89-97 (1994).
Denny, W.A. "Prodrug strategies in cancer therapy." Eur J Med Chem. Jul.-Aug. 2001; 36(7-8):577-95.
Eisenbrand et al., "An Approach Towards More Selective Anticancer Agents," Synthesis, pp. 1246-1258 (1996).
Graf, Laszlo et al., "Electrostatic complementarity within the substrate-binding pocket of trypsin," Proc. Natl. Acad. Sci. USA, vol. 85:4961-4965 (1988).
Harnois-Pontoni, I. et al., "Hydrosoluble Fluorogenic Substrates for Plasmin," Analytic Biochemistry, vol. 193:248-255 (1991).
Hoes and Feijen, "The Application of Drug-Polymer Conjugates in Chemotherapy," in Horizons in Biochemistry and Biophysics, vol. 9: Drug Carrier Systems, pp. 57-109 (1989).
Israel et al., "Adriamycin Analogues. Preparation and Biological Evaluation of Some N-(Trifluoroacetyl)-14-O-[ (N-acetylamino)acyl ] adriamycin Derivatives," J. of Med. Chem., vol. 29:1273-1276 (1986).
Kandukuri, S.P., et al., "Vinblastin-23-oyl Amino Acid Derivatives: Chemistry, Physicochemical Data, Toxicity and Antitumor Activities against P388 and L1210 Leukemias," Journal of Medicinal Chemistry, vol. 28(8):1079-1088 (1985).
Kennett, C.N., et al. "Comparative histochemical, biochemical and immunocytochemical studies of cathepsin B in human gingiva." J Periodontal Res. May 1994; 29(3):203-13.
Kennett et al., "Comparative Histochemical, Biochemical and Immunocytochemical Studies of Cathepsin B in Human Gingiva," Chem. Abstr., #121:79924 (1994).
Masquelier et al., "Amino Acid adn Dipeptide Derivatives of Daunorubicin. 1. Synthesis, Physicochemical Properties, and Lysosomal Digestion," J. Med. Chem., vol. 23:1166-1170 (1980).
Masquelier et al., "Antitumor Activity of Daunorubicin Linked to Proteins: Biological and Antitumor Properties of Peptidic Derivatives of Daunorubicin Used as Intermediates," Chem. Abstr., #97:150635 (1982).
Masquelier et al., "Antitumor Activity of Daunorubicin Linked to Proteins: Biological and Antitumor Properties of Peptidic Derivatives of Daunorubicin Used as Intermediates," Curr. Chemo. and Immunotherapy, Proc. of the 12th Intl. Congress of Chemotherapy, vol. 2:1425-1432 (1982).
Mayer, R. et al., "Peptide Derivatives Specific for a Plasmodium falciparum Proteinase Inhibit the Human Erythrocyte Invasion by Merozoites," Journal of Medicinal Chemistry, vol. 34:3029-3038 (1991).
Moss, J. "Peptide Prodrugs Designed to Limit Metabolism." Washington DC. Am. Chem. Soc. 1995. Chapters 18, pp. 423-445.
Nestor, J.J. "Improved Duration of Action of Peptide Drugs." Washington DC. Am. Chem. Soc. 1995. p. 449-71.
Nishino, Norikazu et al., "Construction of a-Helix Super-Secondary Structure on Various Divalent Anchors by the Leu-Zipper Motif," Peptide Chemistry, Protein Research Foundation, pp. 401-404 (1991).
Pan, C., et al. "CD10 is a key enzyme involved in the activation of tumor-activated peptide prodrug CPI-0004Na and novel analogues: implications for the design of novel peptide prodrugs for the therapy of CD10+ tumors." Cancer Res. Sep. 1, 2003; 63(17):5526-31.
Pozsgay, M. et al., "A Method for Desigining Peptide Substrates for Proteases: Tripeptidal-p-nitroanilide Substrates for Subtilisin Carlsberg," European Journal of Biochemistry, vol. 95:115-119 (1979).
Said et al., "Systemic Treatment: Methotrexate," Clinics in Dermatology, vol. 15:781-797 (1997).
Seitz et al., "Synthesis and Chemical Properties of a Series of Doxorubicin Enaminomalonyl-. b-Alanine Derivatives," Tetrahedron Lett., vol. 3(9):1413-1416 (1995).

Strauss, A.W. et al., "Characterization of an endopeptidase involved in pre-protein processing," Proc. Natl. Acad. Sci. USA, vol. 76(9):4225-4229 (1979).
Taylor & Amidon (eds.) Peptide-Based Drug Design, Controlling Transport and Metabolism, pp. 423-445 and 449-467 (1995).
Trail, P.A. et al., "Cure of Xenografted Human Carcinomas by BR96-Doxorubicin Immunoconjugates," Science, vol. 261:212-215 (1993).
Trouet et al., "A Covalent Linkage between Daunorubicin and Proteins That Is Stable in Serum and Reversible by Lysosomal Hydrolases, as Required for a Lysosomotropic Drug-Carrier Conjugate: In Vitro and In Vivo Studies," Proc. Natl. Acad. Sci., USA, vol. 79:626-629 (1982).
Tugwell et al., "Methotrexate in Rheumatoid Arthritis," Ann. Internal Med., vol. 107:358-366 (1987).
Voet, Donald et al., "Introduction to Enzymes," Biochemistry, 2nd Edition, John Wiley & Sons, Inc., New York, pgs. Chpt. 12, pp. 332-337 (1995).
Whalley, "Receptors Mediating the Increase in Vascular Permeability to Kinins: Comparative Studies in Rat, Guinea Pig and Rabbit," Chem. Abstr. #107:127965 (1987).
Opposition to AU 694546, Notice of Opposition, dated Oct. 23, 1998.
Opposition to AU 694546, Statement of Grounds and Particulars on behalf of Opponent MErck & Co., Inc., dated Jan. 25, 1999.
Opposition to AU 694546, Declaration of Andrew Lee on behalf of Opponent Merck & Co., Inc., executed Jul. 15, 1999 (including Exhibits D1 to D33).
Opposition to AU 694546, Declaration of Veronika Judit Bender on behalf of Opponent Merck & Co., Inc., executed Mar. 14, 2000 (including Exhibits VJB-1, VJB-3 to VJB-10).
Opposition to AU 694546, Declaration of Geoffrey William Tregear on behalf of Opponent Merck 7 Co., Inc., executed on Apr. 26, 2000 (including Exhibit GWT-1).
Opposition to AU 694546, Declaration of David Courtland Heimbrook on behalf of Opponent Merck & Co., Inc., executed Apr. 20, 2000 (including Exhibit DCH-1).
Opposition to AU 694546, Letter to the Commissioner of Patents, IP Australia, from Geoff Davidson, Halford & Co., enclosing Evidence in Answer on behalf of applicants La Region Wallone and Universite Catholique De Louvain, dated Aug. 27, 2001.
Opposition to AU 694546, Statutory Declaration of Geoffrey Allan Pietersz on behalf of Applicants La Region Wallone and Universite De Louvain, executed Aug. 24, 2001 (including Exhibits GAP-1 to GAP-6).
Opposition to AU 694546, Evidence-in-Reply, vol. 1, Statutory Declaration of Gerard Robert Kieczykowski on behalf of Opponent Merck & Co., Inc., executed Jun. 10, 2002 (including Exhibits GRK-1 and GRK-2).
Opposition to AU 694546, Evidence-in-Reply, vol. 1, Statutory Declaration of Maria A. Bednarek on behalf of Opponent Merck & Co., Inc., executed on Jun. 11, 2002 (including Exhibits MAB-1 and MAB-2).
Opposition to AU 694546, Evidence-in-Reply, vol. 1, Statutory Declaration of James V. Pivnichny on behalf of Opponent Merck & Co., Inc., executed Jun. 10, 2002 (including JVP-1 to JVP-3).
Opposition to AU 694546, Evidence-in-Reply, Statutory Declaration of David Courtland Heimbrook on behalf of Merck & Co., Inc., executed on Oct. 21, 2002.
Opposition to AU 694546, Evidence-in-Reply, vol. 2, Statutory Declaration of Veronika Judit Bender on behalf of Opponent Merck & Co., Inc., executed Nov. 26, 2002 (including Exhibits JVB-11 to JVB-22).
Opposition to AU 694546, Letter to Halford & Co., from Jan Morrison, Senior Opposition Officer, IP Australia, reporting on withdrawal of opposition, dated Dec. 3, 2003.
Opposition to NZ 291368, Notice of Opposition to Grant of Patent (Section 21), dated Jul. 23, 1999.
Opposition to NZ 291368, Amended Notice to Opposition to Grant of Patent (Section 21), dated Oct. 26, 1999.
Opposition to NZ 291368, Statement of Case on behalf of Opponent Merck & Co., Inc., filed Oct. 26, 1999.
Opposition to NZ 291368, Additional Submission to The Commissioner, Intellectual Property Office of New Zealand on behalf of Opponent Merck & Co., Inc., dated Nov. 5, 1999.

Opposition to Nz 291368, Counterstatement, filed May 1, 2000.

Opposition to NZ 291368, Declaration of Diana Brown on behalf of Opponent Merck & Co., Inc., executed Jul. 24, 2001 (including DB-1 to DB-4).

Opposition to NZ 291368, Declaration of Maria A. Bednarek on behalf of Opponent Merck & Co., Inc., executed Jul. 25, 2001 (including Exhibits MAB-1 and MAB-2).

Opposition to NZ 291368, Declaration of James V. Pivnichny on behalf of Opponent Merck & Co., Inc., executed Jul. 25, 2001 (including Exhibits JVP-1 to JVP-3).

Opposition to NZ 291368, Declaration of Gerard Robert Kieczykowski on behalf of Opponent Merck & Co., Inc., executed Jul. 26, 2001 (including Exhibit GRK-1 and GRK-2).

Opposition to NZ 291368, Declaration of David Courtland Heimbrook on behalf of Opponent Merck & Co., Inc., executed Jul. 26, 2001 (including DCH-1 to DCH-2).

Opposition to NZ 291368, Statutory Declaration of Veronika Judit Bender on behalf of Opponent Merck & Co., Inc., executed Jul. 30, 2001 (including Exhibits VJB-1 to VJB-7).

Opposition to NZ 291368, Declaration of Geoffrey A. Pietersz on behalf of Applicants La Region Wallone and Universite Catholique De Louvain, executed on Dec. 5, 2002 (including Exhibits GAP-1 to GAP-6).

Opposition to NZ 291368, Letter to The Commissioner, Intellectual Property of New Zealand, from Thomas H. Syddall, AJ Park, advising of opposition withdrawal, dated Dec. 4, 2003.

Opposition to NZ 291368, Letter to Phillips Ormonde & Fitzpatrick, and AJ Park, from The Commissioner, Intellectual Property Office of New Zealand, confirming opposition withdrawal, dated Dec. 5, 2003.

Opposition to NZ 291368, Letter to the Commssioner, Intellectual Property Office of New Zealand, confirming non-hearing prior to issuance of decision, dated Dec. 31, 2003.

Opposition to NZ 291368, Decision of The Commissioner, Intellectual Property Office of New Zealand, on the Opposition, dated Feb. 2, 2004.

Canadian Search Report for Application No. 2,203,622, dated Jan. 19, 2006.

International Search Report for Application No. PCT/BE95/00076. dated Jan. 16, 1996.

```
                        SEQUENCE LISTING

<160> NUMBER OF SEQ ID NOS: 13

<210> SEQ ID NO 1
<211> LENGTH: 4
<212> TYPE: PRT
<213> ORGANISM: Artificial Sequence
<220> FEATURE:
<223> OTHER INFORMATION: a terminal group, beta-alanine, plus a peptide
      arm plus a therapeutic agent, daunorubicin
<220> FEATURE:
<221> NAME/KEY: MISC_FEATURE
<222> LOCATION: (1)..(1)
<223> OTHER INFORMATION: beta-Ala
<220> FEATURE:
<221> NAME/KEY: MISC_FEATURE
<222> LOCATION: (4)..(4)
<223> OTHER INFORMATION: Leu-Daunorubicin

<400> SEQUENCE: 1

Xaa Leu Ala Xaa
1

<210> SEQ ID NO 2
<211> LENGTH: 4
<212> TYPE: PRT
<213> ORGANISM: Artificial Sequence
<220> FEATURE:
<223> OTHER INFORMATION: a terminal group, beta-alanine, plus a peptide
      arm plus a therapeutic agent, doxorubicin
<220> FEATURE:
<221> NAME/KEY: MISC_FEATURE
<222> LOCATION: (1)..(1)
<223> OTHER INFORMATION: beta-Ala
<220> FEATURE:
<221> NAME/KEY: MISC_FEATURE
<222> LOCATION: (4)..(4)
<223> OTHER INFORMATION: Leu-Doxorubicin

<400> SEQUENCE: 2

Xaa Leu Ala Xaa
1

<210> SEQ ID NO 3
<211> LENGTH: 4
<212> TYPE: PRT
<213> ORGANISM: Artificial Sequence
<220> FEATURE:
<223> OTHER INFORMATION: a terminal group, beta-alanine, plus a peptide
      arm plus a therapeutic agent, daunorubicin
<220> FEATURE:
<221> NAME/KEY: MISC_FEATURE
<222> LOCATION: (1)..(1)
<223> OTHER INFORMATION: beta-Ala
<220> FEATURE:
<221> NAME/KEY: MISC_FEATURE
<222> LOCATION: (4)..(4)
```

```
<223> OTHER INFORMATION: Phe-Daunorubicin

<400> SEQUENCE: 3

Xaa Ala Leu Xaa
1

<210> SEQ ID NO 4
<211> LENGTH: 4
<212> TYPE: PRT
<213> ORGANISM: Artificial Sequence
<220> FEATURE:
<223> OTHER INFORMATION: a terminal group, beta-alanine, plus a peptide
      arm plus a therapeutic agent, doxorubicin
<220> FEATURE:
<221> NAME/KEY: MISC_FEATURE
<222> LOCATION: (1)..(1)
<223> OTHER INFORMATION: beta-Ala
<220> FEATURE:
<221> NAME/KEY: MISC_FEATURE
<222> LOCATION: (4)..(4)
<223> OTHER INFORMATION: Phe-Doxorubicin

<400> SEQUENCE: 4

Xaa Ala Leu Xaa
1

<210> SEQ ID NO 5
<211> LENGTH: 4
<212> TYPE: PRT
<213> ORGANISM: Artificial Sequence
<220> FEATURE:
<223> OTHER INFORMATION: a peptide arm plus a therapeutic agent,
      daunorubicin
<220> FEATURE:
<221> NAME/KEY: MISC_FEATURE
<222> LOCATION: (4)..(4)
<223> OTHER INFORMATION: Leu-Daunorubicin

<400> SEQUENCE: 5

Ala Leu Ala Xaa
1

<210> SEQ ID NO 6
<211> LENGTH: 4
<212> TYPE: PRT
<213> ORGANISM: Artificial Sequence
<220> FEATURE:
<223> OTHER INFORMATION: a peptide arm plus a therapeutic agent,
      daunorubicin
<220> FEATURE:
<221> NAME/KEY: MISC_FEATURE
<222> LOCATION: (4)..(4)
<223> OTHER INFORMATION: Leu-Daunorubicin

<400> SEQUENCE: 6

Ala Leu Gly Xaa
1

<210> SEQ ID NO 7
<211> LENGTH: 4
<212> TYPE: PRT
<213> ORGANISM: Artificial Sequence
<220> FEATURE:
<223> OTHER INFORMATION: a peptide arm plus a therapeutic agent,
      daunorubicin
<220> FEATURE:
<221> NAME/KEY: MISC_FEATURE
<222> LOCATION: (4)..(4)
<223> OTHER INFORMATION: Leu-Daunorubicin

<400> SEQUENCE: 7
```

```
Gly Leu Gly Xaa
1

<210> SEQ ID NO 8
<211> LENGTH: 4
<212> TYPE: PRT
<213> ORGANISM: Artificial Sequence
<220> FEATURE:
<223> OTHER INFORMATION: a terminal group, succ-alanine, plus a peptide
      arm plus a therapeutic agent, daunorubicin
<220> FEATURE:
<221> NAME/KEY: MISC_FEATURE
<222> LOCATION: (1)..(1)
<223> OTHER INFORMATION: Succinyl-Ala
<220> FEATURE:
<221> NAME/KEY: MISC_FEATURE
<222> LOCATION: (4)..(4)
<223> OTHER INFORMATION: Leu-Daunorubicin

<400> SEQUENCE: 8

Xaa Leu Ala Xaa
1

<210> SEQ ID NO 9
<211> LENGTH: 5
<212> TYPE: PRT
<213> ORGANISM: Artificial Sequence
<220> FEATURE:
<223> OTHER INFORMATION: a terminal group, p-glutamate, plus a peptide
      arm plus a therapeutic agent, doxorubicin
<220> FEATURE:
<221> NAME/KEY: MISC_FEATURE
<222> LOCATION: (1)..(1)
<223> OTHER INFORMATION: pGlu
<220> FEATURE:
<221> NAME/KEY: MISC_FEATURE
<222> LOCATION: (5)..(5)
<223> OTHER INFORMATION: Leu-Doxorubicin

<400> SEQUENCE: 9

Xaa Ala Leu Ala Xaa
1               5

<210> SEQ ID NO 10
<211> LENGTH: 4
<212> TYPE: PRT
<213> ORGANISM: Artificial Sequence
<220> FEATURE:
<223> OTHER INFORMATION: a terminal group, D-alanine, plus a peptide arm
      plus a therapeutic agent, daunorubicin
<220> FEATURE:
<221> NAME/KEY: MISC_FEATURE
<222> LOCATION: (1)..(1)
<223> OTHER INFORMATION: D-Ala
<220> FEATURE:
<221> NAME/KEY: MISC_FEATURE
<222> LOCATION: (4)..(4)
<223> OTHER INFORMATION: Leu-Daunorubicin

<400> SEQUENCE: 10

Xaa Leu Ala Xaa
1

<210> SEQ ID NO 11
<211> LENGTH: 5
<212> TYPE: PRT
<213> ORGANISM: Artificial Sequence
<220> FEATURE:
<223> OTHER INFORMATION: a terminal group, D-leucine, plus a peptide arm
      plus a therapeutic agent, daunorubicin
<220> FEATURE:
<221> NAME/KEY: MISC_FEATURE
<222> LOCATION: (1)..(1)
```

```
<223> OTHER INFORMATION: D-Leu
<220> FEATURE:
<221> NAME/KEY: MISC_FEATURE
<222> LOCATION: (5)..(5)
<223> OTHER INFORMATION: Leu-Daunorubicin

<400> SEQUENCE: 11

Xaa Ala Leu Ala Xaa
1               5

<210> SEQ ID NO 12
<211> LENGTH: 5
<212> TYPE: PRT
<213> ORGANISM: Artificial Sequence
<220> FEATURE:
<223> OTHER INFORMATION: a terminal group, D-leucine, plus a peptide arm
      plus a therapeutic agent, daunorubicin
<220> FEATURE:
<221> NAME/KEY: MISC_FEATURE
<222> LOCATION: (1)..(1)
<223> OTHER INFORMATION: D-Leu
<220> FEATURE:
<221> NAME/KEY: MISC_FEATURE
<222> LOCATION: (2)..(2)
<223> OTHER INFORMATION: D-Ala
<220> FEATURE:
<221> NAME/KEY: MISC_FEATURE
<222> LOCATION: (5)..(5)
<223> OTHER INFORMATION: Leu-Daunorubicin

<400> SEQUENCE: 12

Xaa Xaa Leu Ala Xaa
1               5

<210> SEQ ID NO 13
<211> LENGTH: 4
<212> TYPE: PRT
<213> ORGANISM: Artificial Sequence
<220> FEATURE:
<223> OTHER INFORMATION: a terminal group, beta-alanine, plus a peptide
      arm plus a therapeutic agent, coumarin
<220> FEATURE:
<221> NAME/KEY: MISC_FEATURE
<222> LOCATION: (1)..(1)
<223> OTHER INFORMATION: beta-Ala
<220> FEATURE:
<221> NAME/KEY: MISC_FEATURE
<222> LOCATION: (4)..(4)
<223> OTHER INFORMATION: Leu-Coumarin

<400> SEQUENCE: 13

Xaa Leu Ala Xaa
1
```

TUMOR-ACTIVATED PRODRUG COMPOUNDS AND TREATMENT

RELATED APPLICATIONS

This application is a divisional application of U.S. Ser. No. 11/370,290, filed Mar. 8, 2006 (now U.S. Pat. No. 7,390,629, issued Jun. 24, 2008); which is a divisional application of U.S. Ser. No. 10/012,576, filed Nov. 9, 2001 (now U.S. Pat. No. 7,037,898, issued May 2, 2006); which is a continuation application of U.S. Ser. No. 09/298,330, filed Apr. 23, 1999 (now U.S. Pat. No. 6,342,480, issued Jan. 29, 2002); which is a continuation application of No. 08/793,910, filed Apr. 1, 1997 (now U.S. Pat. No. 5,962,216, issued Oct. 5, 1999); which is a national phase application of PCT/BE95/00076, filed Aug. 21, 1995; which claims priority to Belgium applications BE 9400751, filed Aug. 19, 1994 and BE 9400752, filed Aug. 19, 1994. The contents of each of the aforementioned applications and patents are hereby incorporated by reference in their entirety.

SUBJECT OF THE INVENTION

The present invention relates to new compounds, to the pharmaceutical composition and the diagnostic device comprising them and to their use for the preparation of medicinal products intended for the treatment and/or for the diagnosis of cancerous tumors and/or of inflammatory reactions.

PRIOR ART AND TECHNOLOGICAL BACKGROUND UNDERLYING THE INVENTION

Many tumor agents, such as anthracyclines and vinca alkaloids, have been developed in the last few years and are especially effective for the treatment of cancers. However, these molecules are often characterized in vivo by an acute toxicity, especially a marrow and mucosal toxicity, as well as a chronic cardiac toxicity in the case of the anthracyclines and chronic neurological toxicity in the case of the vinca alkaloids.

Thus, it has been sought to develop more specific antitumor agents, so that they are more effective against tumor cells, and consequently to decrease the side effects of these products (toxicity, destruction of non-tumor cells, etc.).

U.S. Pat. No. 4,296,105 describes doxorubicin derivatives linked to an optionally substituted amino acid, which possess in vitro a higher antitumor activity and lower toxicity than doxorubicin.

However, since these derivatives have an intracellular action site, these molecules are still liable to enter tumor cells and normal cells.

Thus, in the last few years, new therapeutic agents have been proposed in the form of prodrugs.

Prodrugs are molecules capable of being converted to drugs (active therapeutic compounds) by certain chemical or enzymatic modifications of their structure.

However, these prodrugs are also characterized by a low stability in the blood and serum, which contain enzymes which inactivate these molecules.

The documents Chemical Abstract 97:150635, Journal of Medicinal Chemistry, Vol. 23, pp. 1171-1174 (1980); Drugs Exp. Clin., Vol. 9, pp. 303-311 (1983); Journal of Medical Chemistry, Vol. 23, pp. 1166-1170 (1980) and Patent Application BE-882.541 describe prodrugs comprising a carrier linked to the drug via a peptide arm. Preferably, the arm consists of four amino acids and is linked via its free carboxyl function to the free amine function of derivatives of anthracyclines such as daunorubicin.

In addition, the arm of these prodrugs is linked via its free amine function to a carrier consisting of a macromolecule (protein such as BSA, immunoglobulins, etc.) which permits the selective endocytosis of the prodrug by target cells.

It is also known that methotrexate may be used for the treatment of inflammatory reactions such as rheumatic diseases, but its high toxicity limits its applications.

OBJECTS OF THE INVENTION

The present invention is directed towards providing new compounds comprising an antitumor therapeutic agent or a marker, especially prodrugs comprising an antitumor therapeutic agent, displaying improved therapeutic properties relative to the products of the prior art, especially improved therapeutic properties in the treatment of cancerous tumors and/or in the treatment of inflammatory reactions such as rheumatic diseases.

A particular object of the present invention is directed towards obtaining prodrugs which display a high specificity of action, a reduced toxicity and an improved stability in the serum and blood.

A further object of the present invention is directed towards obtaining compounds comprising a marker enabling tumors to be characterized (diagnosis, progression of the tumor, assay of the factors secreted by tumor cells, etc.).

Characteristic Features of the Present Invention.

The present invention relates to compounds (W-Z-M) comprising a component chosen from the group consisting of markers and therapeutic agents, preferably those having antitumor and/or anti-inflammatory activity, possessing an intracellular active site (A.S.), linked to a ligand (W-Z) comprising an arm (Z) linked to a terminal group (W), in which the linkage between the arm (Z) of the ligand (W-Z) and the component (M) prevents cellular entry of the compound (W-Z-M) and/or inhibits expression of the marker (M); in which this linkage can be selectively cleaved by factors secreted by target cells, so as to permit expression of the marker (M) and/or entry of the therapeutic agent (M) into said target cells, and in which the terminal group (W) provides for the stability of the compound (W-Z-M) in the serum and in the circulating blood.

Factors secreted by target cells, especially by tumor cells and cells involved in inflammatory reactions (macrophages, monocytes, etc.), are understood to mean enzymes such as proteases or peptidases, secreted specifically into the extracellular medium by said cells.

These enzymes are hence capable of selectively cleaving the linkage existing between the component (M) and the arm (Z) of the ligand (W-Z) so as to permit expression of the marker (advantageously in the environment of said cells) and/or entry of the therapeutic agent preferentially into said cells, and of effecting their destruction in this way and/or of blocking their proliferation.

The linkage between the terminal group (W) and the arm (Z) and also the linkage between the arm (Z) and the component (M) may be any type of covalent linkage which does not affect the properties of the compound (W-Z-M) according to the invention.

Linkage between the arm (Z) of the ligand (W-Z) and the marker (M) inhibiting expression of the marker (M) is understood to mean any covalent linkage which prevents the detection and/or quantification of the marker (M).

The expression of the free marker (M) may be detected by any method or device well known to a person skilled in the art, for example by detection by staining, fluorescence, bioluminescence, chemoluminescence, etc., optionally involving one or more intermediate reagents.

Preferably, said marker is chosen from the group consisting of coumarin, 7-amido-4-(trifluoromethyl)coumarin, para-nitroanilide (which may be characterized in its free form by colorimetry after a diazotization reaction), β-naphthylamide and 4-methoxy-β-naphthylamide, and is capable of being detected by fluorescence when it is no longer linked to the ligand (W-Z).

Terminal group (W) providing for the stability of the compound according to the invention in the serum and in the circulating blood is understood to mean any group which reduces or inhibits the cleavage of the compound according to the invention in the serum and the circulating blood, especially which reduces or inhibits the hydrolysis of the compound according to the invention by proteinases and peptidases present in the serum and/or the circulating blood, especially the peptidases and proteinases associated with the red cells.

In particular, a terminal group (W) provides for the stability of the compound of the invention when less than 20%, and preferably less than 2%, of the compound is cleaved by said enzymes during its storage in human blood at 37 C for more than 2 hours.

Preferably, this terminal group (W) is chosen from the group consisting of amino acids not present in mammals (that is to say amino acids which cannot be genetically encoded by mammals) or a succinyl group.

According to a preferred embodiment of the invention, the group (W) is β-Alanine of formula: $NH_2-CH_2-CH_2-COOH$, linked via its carboxyl function to the arm (Z).

The arm (Z) can consist of any chemical structure (polysaccharides, peptides, etc.) whose linkage to the component (M) is capable of being selectively cleaved by the factors secreted by the target cells so as to permit expression of the marker (M) in the environment of said cells and/or entry of the therapeutic agent (M) preferentially into said cells.

According to the invention, the linkage between the component (M) and the arm (Z) of the ligand (W-Z) consists of a peptide link. Preferably, the arm (Z) is a peptide consisting of at least two optionally substituted amino acids.

The arm (Z) of the ligand (W-Z) preferably consists of the following succession of amino acids: L-leucyl-L-alanyl-L-leucyl, L-leucyl-L-alanyl or L-alanyl-L-leucyl-L-phenylalanyl or L-alanyl-L-leucyl, linked via their carboxyl function to the component (M).

According to the invention, the therapeutic agent (M) is either a therapeutic agent used in cancer chemotherapy, preferably chosen from the therapeutic agents described by Bruce A. Chabner and Jerry M. Collins (Cancer Chemotherapy, Lippincott Ed., ISBN 0-397-50900-6 (1990)), or an anti-inflammatory such as methotrexate; and capable of binding to the ligand (W-Z), preferably via a peptide link to the group (Z) of the ligand (W-Z).

In particular, the therapeutic agent is chosen from the group consisting of anthracyclines, folic acid derivatives, vinca alkaloids, mitoxantrone, calicheamycin, cytosine arabinoside (ARA-C), adenosine arabinoside (ARA-A), fludarabine phosphate, melphalan, bleomycin, mitomycin, L-canavanine, taxoids, camptothecin and their derivatives, especially TOPOTECAN® (9-dimethylaminomethyl-10-hydroxy-camptothecin hydrochloride), and derivatives of fluorochromes such as rhodamine 123 and its derivatives, especially rhodamine isothiocyanates, optionally linked to a substituted or unsubstituted amino acid. The substitution on the amino acid can be any substitution which does not affect the properties of the compound (W-Z-M) according to the invention.

Derivatives of these molecules are understood to mean said molecules modified with a chemical group enabling them to be bound to the arm (Z) of the ligand (W-Z) via a covalent link which does not affect the therapeutic activity of the original molecule.

Preferably, in the compounds of the invention, the therapeutic agent (M) is chosen from the group of anthracyclines, especially doxorubicin (DOX) and daunorubicin (DNR), optionally linked to a substituted or unsubstituted amino acid.

Advantageously, the therapeutic agent corresponds to the general formula:

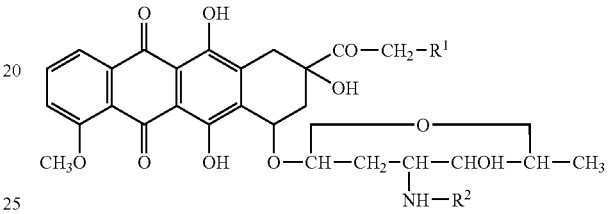

(Formula I)

in which:
R$^1$ is a hydrogen atom or an OH group,
R$^2$ is a hydrogen atom or a radical of formula

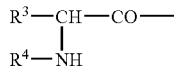

(Formula II)

in which:
R$^3$ is a hydrogen atom or an optionally substituted alkyl radical,
R$^4$ represents a hydrogen atom or forms with R$^3$ an alkylene radical containing 3 or 4 carbon atoms.
Preferably, R$^2$ is a radical of formula:

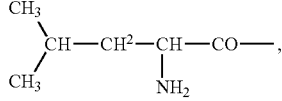

(Formula III)

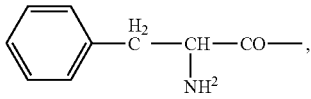

(Formula IV)

or one of their isomers.

According to a preferred embodiment of the invention, the compound is β-alanyl-L-leucyl-L-alanyl-L-leucyldaunorubicin (hereinafter identified throughout by βAla-Leu-Ala-Leu-DNR (SEQ ID NO:1)), β-alanyl-L-leucyl-L-alanyl-L-leucyl-doxorubicin (hereinafter identified throughout by βAla-Leu-Ala-Leu-DOX (SEQ ID NO:2)), β-alanyl-L-alanyl-L-leucyl-L-phenylalanyldaunorubicin (hereinafter identified throughout by βAla-Ala-Leu-Phe-DNR (SEQ ID NO:3)) or β-alanyl-L-alanyl-L-leucyl-L-phenylalanyldoxorubicin (hereinafter identified throughout by βAla-Ala-Leu-Phe-DOX (SEQ ID NO:4)).

The present invention also relates to the pharmaceutical composition comprising the compound according to the invention and optionally a pharmaceutically acceptable adjuvant or vehicle.

These compositions may, for example, be administered parenterally or intravenously. The compositions according to the invention for parenteral administration can be, in particular, sterile solutions, aqueous or nonaqueous, suspensions or emulsions. As a pharmaceutically acceptable solvent or vehicle, propylene glycol, polyethylene glycol, injectable organic esters, for example ethyl oleate, or cyclodextrins may be employed. These compositions can also comprise wetting, emulsifying and/or dispersing agents.

The sterilization may be carried out in several ways, for example using a bacteriological filter, by incorporating sterilizing agents in the composition or by irradiation. They may also be prepared in the form of sterile solid compositions which may be dissolved at the time of use in sterile water or any other sterile injectable medium.

The present invention can also comprise adjuvants which are well known to a person skilled in the art (vitamin C, antioxidant agents, etc.) capable of being used in synergy with the compound according to the invention in order to improve and prolong the treatment of cancerous tumors.

The minimum doses for administration of the compounds according to the invention to a patient are the usual doses of the abovementioned antitumor therapeutic agents, as are described, in particular, by Bruce A. Chabner and Jerry M. Collins (Cancer Chemotherapy, Lippincott Ed., ISBN 0-397-50900-6 (1990)) or higher administration doses.

The doses administered hence vary in accordance with the therapeutic agent used for the preparation of the compound according to the invention.

The present invention relates to the use of the pharmaceutical composition according to the invention for the preparation of a medicinal product intended for the treatment of cancerous tumors, as well as to a method for the therapeutic treatment of cancerous tumors, consisting in administering, especially parenterally or intravenously, the pharmaceutical composition according to the invention to a patient.

The present invention also relates to the use of the pharmaceutical composition according to the invention for the preparation of a medicinal product intended for the treatment of inflammatory reactions, especially rheumatic diseases, as well as to a method for the therapeutic treatment of inflammatory reactions, especially rheumatic diseases, consisting in administering, especially parenterally or intravenously, the pharmaceutical composition according to the invention, especially a pharmaceutical composition comprising a compound according to the invention in which the therapeutic agent (M) is methotrexate or a methotrexate derivative, to a patient.

Another aspect of the present invention relates to a device for diagnosis and/or for assay, comprising the compound according to the invention, especially the compound comprising coumarin as marker.

DESCRIPTION OF A PREFERRED EMBODIMENT OF THE INVENTION

The present invention is based on the unexpected discovery that it is possible to make a marker or a therapeutic agent (M), especially an antitumor and/or anti-inflammatory therapeutic agent, inactive by linkage with a ligand (W-Z) which inhibits expression of the marker or prevents intracellular entry of the therapeutic agent (M) into normal cells (N.C.) and target cells (T.C.).

According to the invention, said target cells are tumor cells or cells participating in anti-inflammatory reactions, especially those associated with rheumatic diseases, such as macrophages, monocytes, etc.

Figure 1:
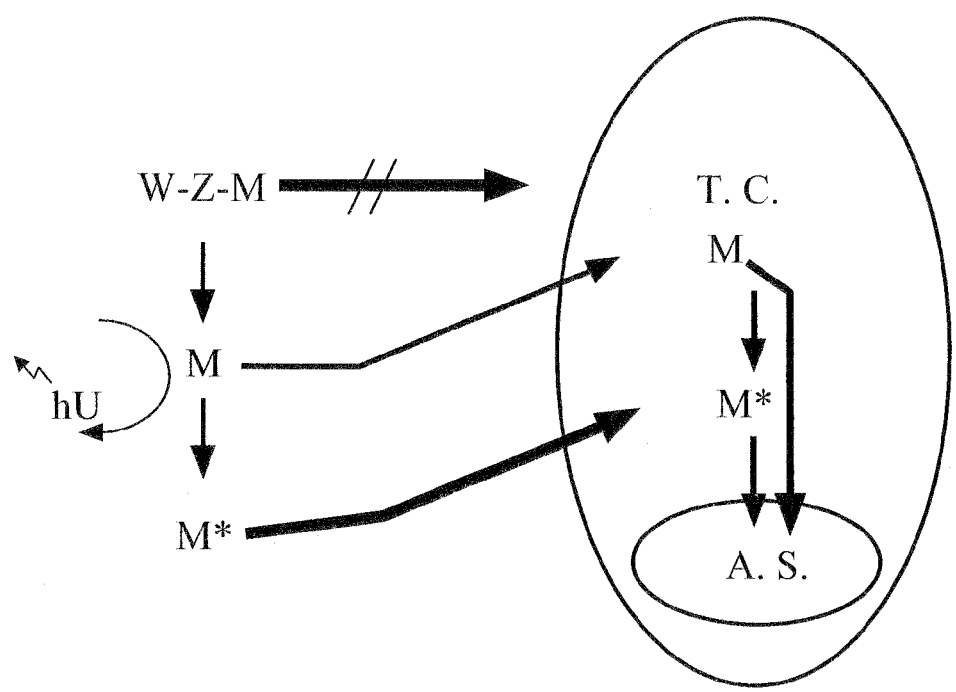
FIG. 1 shows the mechanism of action of the compound according to the invention on its action site (A.S.) in a target cell (T.C.).

Unexpectedly, the target cells (T.C.) liberate into the extracellular medium enzymes such as proteases or peptidases which are capable of selectively hydrolyzing a covalent linkage between the arm (Z) of the ligand (W-Z) and the marker (M) or the therapeutic agent (M), so as to permit expression of the marker (M) or entry of the therapeutic agent (M) into said target cells (T.C.). In the target cell, the therapeutic agent (M) acts either directly on its specific intracellular action site (A.S.) or, after a modification under the action of intracellular proteases, is modified to another therapeutic Agent (M*) and kills the target cell (T.C.) or blocks its proliferation (FIG. 1).

Figure 2:
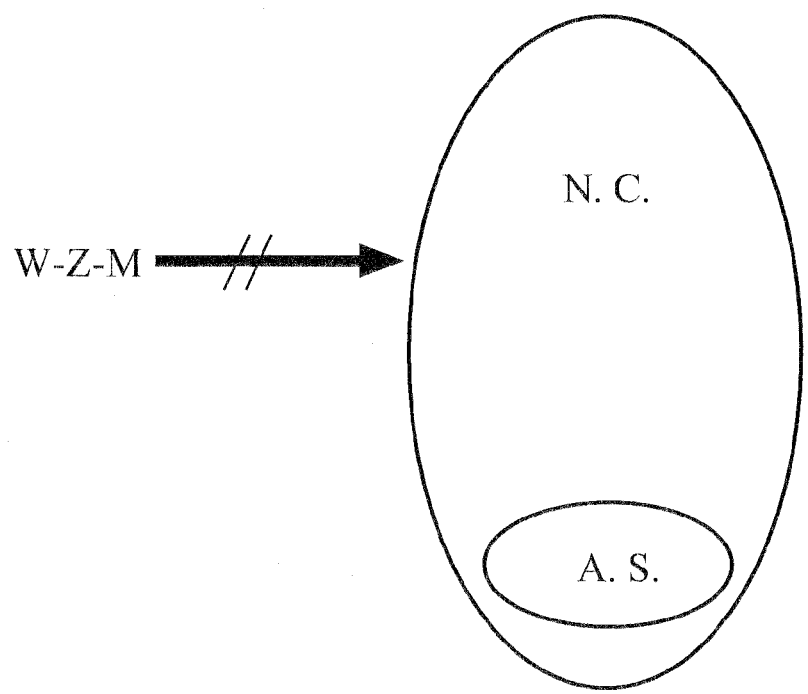
FIG. 2 shows the mechanism of action of the compound according to the invention in a normal cell (N.C.).

Since normal cells liberate little or none of said enzymes in vivo, the compound according to the invention is maintained inactive and does not enter the normal cells (FIG. 2).

In particular, expression of the marker (via an intermediate, for example emitting light) enables cancer cells to be characterized, thereby improving the diagnosis of the cancer, the study of the progression of the tumor, the assay of the factors secreted by the tumor cells, etc.

The compound described in the present patent application corresponds to this mechanism of action, since it satisfies the criteria needed for it to be administered effectively:

1. The therapeutic agent (M):
   possesses an intracellular action site,
   a high specific activity,
   a chemical group permitting covalent linkage with a ligand (W-Z);
   if the requisite chemical group is not essential to the activity of the therapeutic agent (M), it does not have to be restored intact after enzymatic hydrolysis of said covalent linkage.
2. Linkage with the ligand (W-Z) prevents intracellular entry of the therapeutic agent (M) both into normal cells and into the target cells.
3. The compound according to the invention remains stable in the serum and in the blood, and is insensitive to the action of the circulating proteinases and peptidases associated with the red cells.
4. The covalent linkage existing between the therapeutic agent (M) and the ligand (W-Z) is partially or completely degraded by the enzymes secreted by the target cells.
5. The nature of the ligand (W-Z) and its linkage to the marker or to the therapeutic agent (M) are determined in accordance with the enzymes secreted by the target cells.
6. The compound is less toxic in vivo than the starting therapeutic agent. This decrease in toxicity applies, in particular, to the acute effects such as the marrow and mucosal toxicity, as well as the possible cardiac or neurological toxicity.

Anthracycline Derivatives.

The therapeutic agent (M) according to the invention can be an anthracycline derivative, especially doxorubicin, daunorubicin, 4-epidoxorubicin, 4-demethoxydoxorubicin (idarubicin), 4'-tetrahydropyranyldoxorubicin (pirarubicin), caminomycin, esorubicin and 4'-iododoxorubicin.

The ligand (W-Z) is then linked via its carboxyl function to the -amino end of the therapeutic agent.

Folic Acid Derivatives.

The antitumor therapeutic agent can also be a folic acid derivative, especially methotrexate (MTX) or its derivatives, such as lysine (−)-MTX or lysine (−)-MTX as are described by Fitzpatrick et al. (Anti-cancer Drug Design 10, pp. 1-9 and pp. 11-24 (1995)), or aminopterin, especially lysine (−)-AMPT and lysine (−)-AMPT.

The ligand (W-Z) is then linked via its carboxyl function to the -amino end of the therapeutic agent.

Vinca Alkaloid Derivatives.

The vinca alkaloid derivatives according to the present invention are, in particular, derivatives of vinblastine, of vincristine, of vindesine and of navelbine.

A. Linkage at Position 3.
1. Deacetylvincristine acid, which is formed by adding lysine to the -amino group to obtain a lysine ( )-dAcVCR. The ligand (W-Z) is then linked via its carboxyl end to the -amino group of the lysine ( )-dAcVCR.
2. Deacetylvincristine acid may also be obtained by adding an aliphatic diamine to vincristine (NH2-alkyl-NH2) so as to obtain an NH2-alkyl-dAcVCR, the ligand (W-Z) then being linked via its carboxyl end to the -amino group of the lysine ( )-dAcVCR.

Vinblastine (VBL) and navelbine (5'-noranhydrovinblastine) derivatives may be linked to the ligand (W-Z) in the same manner as is described above for vincristine.

B. Linkage at Position 4.
1. $V_4$-hemiaspartate-vincristine is formed from vincristine by linkage of aspartic acid through its -carboxyl group to the hydroxyl group at position 4 of vincristine ($V_4$). The ligand (W-Z) is then linked via its carboxyl end to the -amino group of the $V_4$-hemiaspartate-vincristine.
2. $V_4$-lysylvincristine is formed from vincristine by linking lysine via its -carboxyl group to the hydroxyl group at position 4 of vincristine ($V_4$). The ligand (W-Z) is then linked via its carboxyl end to the -amino group of the $V_4$-lysylvincristine.
3. $V_4$-lysylvincristine is formed from vincristine by linking lysine via its -carboxyl group to the hydroxyl group at position 4 of vincristine ($V_4$). The ligand (W-Z) is then linked via its carboxyl end to the -amino group of the lysine of the $V_4$-lysylvincristine. According to an alternative, the ligand (W-Z) may be linked both to the - and -amino groups of the $V_4$-lysylvincristine.
4. $V_4$-β-Alanylvincristine is formed from vincristine by linking β-Alanyl via its carboxyl group to the hydroxyl group at position 4 of vincristine ($V_4$). The ligand (W-Z) is then linked via its carboxyl end to the amino group of the β-Alanyl of the $V_4$-β-Alanylvincristine.

Vinblastine, vindesine and navelbine derivatives may be linked to the ligand (W-Z) in the same manner as is described above for vincristine.

Calicheamycin Derivatives.

The N-acetyldimethylhydrazide derived from calicheamycin is obtained by reacting a thiol hydrazide with calicheamycin.

The ligand (W-Z) is then linked via its carboxyl end to the N-acetyldimethylhydrazide derived from calicheamycin.

Mitoxantrone Derivatives.

A β-Alanyl derived from mitoxantrone is prepared by linkage of the carboxyl function of β-Alanyl to the hydroxyl side chains of mitoxantrone.

A mono- or bisubstitution is then possible. The ligand (W-Z) is then linked via its carboxyl end to the amino group of the β-Alanylmitoxantrone.

Cytosine Arabinoside (ARA-C) Derivatives.

The ligand (W-Z) is linked via its carboxyl end to the amino group of cytosine arabinoside.

Adenosine Arabinoside (Ara-A) Derivatives.

The ligand (W-Z) is linked via its carboxyl end to the amino group of adenosine arabinoside.

Fludarabine Phosphate Derivatives.

The ligand (W-Z) is linked via its carboxyl end to the amino group of fludarabine phosphate.

Melphalan Derivatives.

The ligand (W-Z) is linked via its carboxyl end to the amino group of melphalan.

Bleomycin Derivatives.

The ligand (W-Z) is linked via its carboxyl end to the amino group of bleomycin, of peplomycin or of liblomycin.

Mitomycin Derivatives.

The ligand (W-Z) is linked via its carboxyl end to the amino group at position 7 of mitomycin.

L-Canavanine Derivatives.

The ligand (W-Z) is linked via its carboxyl end to the -amino group of L-canavanine.

Taxoid Derivatives.

A β-Alanyl derivative of taxol is prepared by linkage of the carboxyl function of β-Alanyl to the hydroxyl side chains at position 7 of taxol.

The hydroxyl group of taxol is reactive but not essential to the antitumor activity of taxol (Nicalaou K. C. et al., Chemistry and Biology of Taxol, Angew. Chem. Int. Ed. Engl. (1994), 33, pp. 15-44).

The ligand (W-Z) is then linked via its carboxyl end to the amino group of the β-Alanyltaxol.

The ligand (W-Z) may be linked in a comparable manner to the derivative β-Alanyltaxotere.

Camptothecin Derivatives.

The ligand (W-Z) is linked via its carboxyl end to the -amino group of 9-aminocamptothecin or of 7-aminomethylcamptothecin.

The present invention will be described in greater, detail in the examples which follow, given by way of non-limiting illustration of the present invention.

EXAMPLE 1

Synthesis of N-L-leucyldaunorubicin (Leu-DNR)

L-Leucyldaunorubicin is synthesized by reacting daunorubicin in base form (DNR) with L-leucine protected on its amine function by an FMOC (fluorenylmethoxycarbonyl) group and in which the carboxyl function is activated with IBCF (isobutyl chloroformate), followed by deprotection of the amine function.

DNR in base form is prepared from 200 mg of daunorubicin hydrochloride (R. Bellon) dissolved in 500 μl of DMF (dimethylformamide) to which 1.2 equivalents of N-methylmorpholine are added.

1.2 equivalents of Fmoc-N-leucine (NOVA BIOCHEM) are dissolved in 500 μl of DMF (dimethylformamide), and 1.2 equivalents of N-methylmorpholine and 1.2 equivalents of IBCF are added at −20 C. After 15 minutes, this solution is added to that of the DNR base, and the mixture is left stirring for 16 hours protected from light.

Fmoc-N-L-Leucyldaunorubicin is precipitated in 150 ml of a 1:1 mixture of ether and petroleum ether (40-60 C) and then filtered off on No. 4 sintered glass. The product is purified by chromatography on a column of silica (70-230 mesh silica Si-60 from E. MERCK) eluted with chloroform. The residual DNR is eluted with 10% methanol. Fractions containing the Fmoc-N-L-leucyl-DNR are concentrated in a rotary evaporator and the product is taken up in 500 μl of DMF. Deprotection is carried out by adding 5 equivalents of diethylamine (LAB SCAN) at −20 C.

After 1 hour, the N-L-leucyl-DNR is precipitated with a 1:1 mixture of ether and petroleum ether (40-60 C) and then filtered off on No. 4 sintered glass. The product is taken up in a chloroform/methanol (4:1 by volume) mixture and the diethylamine is neutralized with one equivalent of HCl.

The product is then purified by chromatography on a column of silica (70-230 mesh silica Si-60 from E. MERCK) eluted with chloroform and then chloroform containing 15% of methanol. Fractions containing the N-L-leucyl-DNR are concentrated in a rotary evaporator, the product is taken up in distilled water and the hydrochloride is formed by adjusting the pH to 7 with 1 N HCl. The product is then filtered through modified silica gel (Seppak C18 from WATERS) and the N-L-leucyldaunorubicin hydrochloride is eluted with methanol and then concentrated in a rotary evaporator. The usual yield is from 70 to 80%.

Characteristics of the Products.

| Compound | Formula | Melting point (C.) | TLC Rf | HPLC Tr |
|---|---|---|---|---|
| DNR | $C_{27}H_{29}NO_{10} \cdot HCl$ | 189 | 0.05 | 0.67 |
| L-Leu-DNR | $C_{33}H_{40}N_2O_{11} \cdot HCl$ | 201 | 0.31 | 0.48 |

TLC Rf: chloroform/methanol/water (120:20:1 by volume) system
HPLC Tr: retention time relative to doxorubicin, HPLC system: Si-60 column eluted with a chloroform/methanol/acetic acid/0.3 mM aqueous $MgCl_2$ sol. (1440:420:80:60 by volume) mixture.

Synthesis of β-L-alanyl-L-leucyl-L-alanine

β-L-Alanyl-L-leucyl-L-alanine is prepared by solid-phase synthesis according to Merrifield's technique (The Chemistry of Polypeptides, (P. G. Katsoyannis Ed.), Plenum Press, New-York, pp. 336-361 (1973)).

Fluorochrome Derivatives.

The ligand (W-Z) is linked via its carboxyl end to the amino group of rhodamine 123.

Synthesis of β-Ala-Leu-Ala-Leu-DNR

β-Ala-Leu-Ala-Leu-DNR (SEQ ID NO:1) is synthesized by grafting Fmoc-β-L-alanyl-L-leucyl-L-alanine, prepared by solid-phase synthesis, onto N-L-leucyldaunorubicin.

1.5 equivalents (eq.) of N-methylmorpholine and 1.5 eq. of isobutyl chloroformate are added to Fmoc-L-alanyl-L-leucyl-L-alanine (1.5 equivalents) dissolved in DMF. After 10 minutes at −20 C, 1.5 eq. of HOBT are added. Then, after 5 minutes, 1 eq. of N-L-leucyldaunorubicin base dissolved in DMF is added. After reaction, the Fmoc-β-Ala-Leu-Ala-Leu-DNR is precipitated with ether and then deprotected with diethylamine. The β-Ala-Leu-Ala-Leu-DNR (SEQ ID NO:1) is purified by chromatography on a column of silica and the hydrochloride is formed by adding 1 N HCl.

Synthesis of β-Ala-Leu-Ala-Leu-DOX

β-Ala-Leu-Ala-Leu-DOX (SEQ ID NO:2) is synthesized by grafting β-L-alanyl-L-leucyl-L-alanine, prepared by solid-phase synthesis, onto N-L-leucyldoxorubicin, as described for the synthesis of β-Ala-Leu-Ala-Leu-DNR (SEQ ID NO:1).

In this synthesis, the coupling agent (isobutyl chloroformate) may be omitted so as to increase further the production yield of the compound according to the invention in the case of formation of β-Ala-Leu-Ala-Leu-DOX (SEQ ID NO:2).

EXAMPLE 2

Figure 3A:
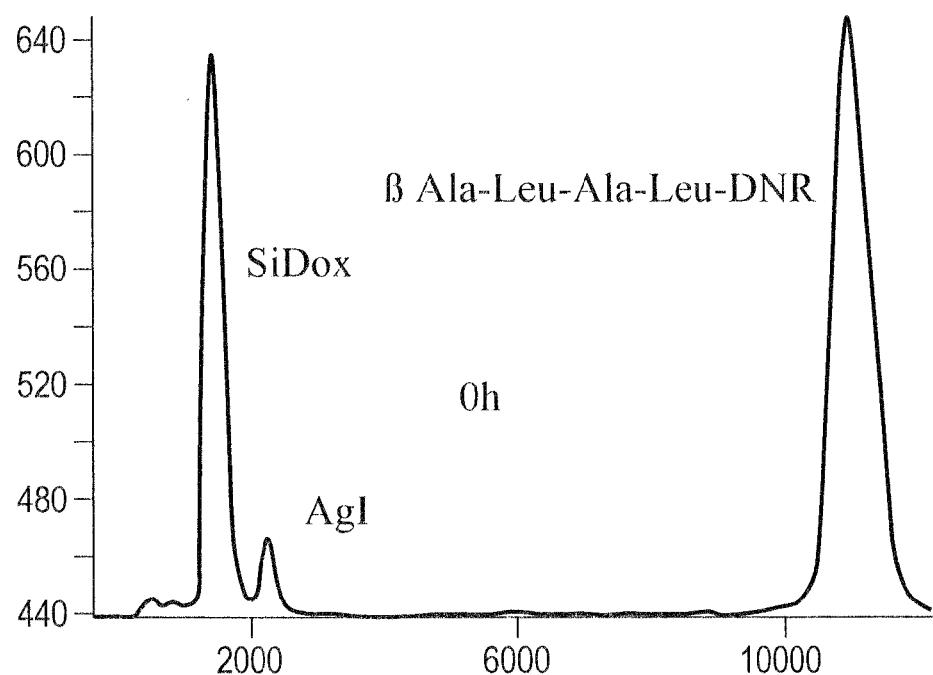
FIG. 3 shows the hydrolysis of β-Ala-Leu-Ala-Leu-daunorubicin (SEQ ID NO:1) in conditioned medium from MCF7/6 human mammary carcinoma cells (chromatogram at time zero (a) and after two hours of incubation (b)).
Figure 3B:
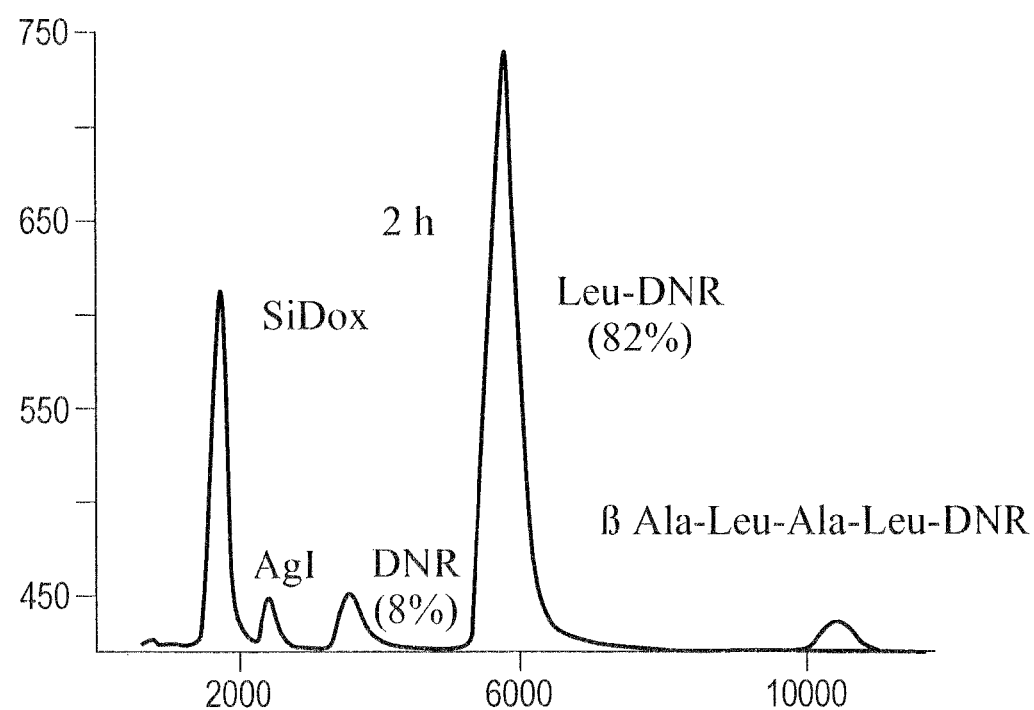

Degradation of 5-Ala-Leu-Ala-Leu-DNR in a Conditioned Medium from MCF7/6 Mammary Carcinoma Cells β-Ala-Leu-Ala-Leu-DNR (SEQ ID NO:1) was incubated at 37 C for 2 hours in conditioned medium from MCF7/6 cells, concentrated 20 of 40 times, and the compound together with the digestion products were extracted at pH 9 and analysed by HPLC (FIG. 3).

| Starting material or Metabolite | Time 0 | After 1 hour | After 2 hours |
|---|---|---|---|
| β-Ala-L-Leu-L-Ala-L-Leu-DNR (SEQ ID NO: 1) | 100% | 10% | 2.6% |
| L-Leu-L-Ala-L-Leu-DNR or DNR | 0% | 3.0% | 7.3% |
| L-Ala-L-Leu-DNR | 0% | <1% | <1% |
| L-Leu-DNR | 0% | 83% | 90% |

It is seen from this that L-Leu-DNR is the major metabolite from the endopeptidase, and that its formation from the prodrug is virtually complete after 1 hour of incubation at 37 C. Under the experimental conditions used, L-Leu-L-Ala-L-Leu-DNR and DNR are not sufficiently well separated for it to be possible to assert confidently that the L-Leu-DNR formed hydrolyses thereafter more slowly to DNR.

EXAMPLE 3

Degradation of β-Ala-Leu-Ala-Leu-DOX in Conditioned Medium from MCF7/6 Mammary Carcinoma Cells When β-Ala-Leu-Ala-Leu-DOX (SEQ ID NO:2) is incubated at 37 C for 2 hours in conditioned medium from MCF7/6 cells, concentrated 20 times, the only metabolites now to be found are L-Leu-DOX and DOX.

| Starting material or Metabolite | Time 0 | After 2 hours |
|---|---|---|
| β-Ala-L-Leu-L-Ala-L-Leu-DOX (SEQ ID NO: 2) | 100% | 23% |
| L-Leu-L-Ala-L-Leu-DOX | 0% | <1% |
| L-Ala-L-Leu-DOX | 0% | <1% |
| L-Leu-DOX | 0% | 68% |
| DOX | 0% | 9% |

β-Ala-Leu-Ala-Leu-DOX (SEQ ID NO:2) is hydrolyzed less rapidly than the DNR prodrug by the peptidase or peptidases secreted by MCF7/6 cells. On the other hand, the conversion of L-Leu-DOX to DOX seems to be a little more extensive than the conversion of L-Leu-DNR to DNR.

EXAMPLE 4

Degradation of β-Ala-Leu-Ala-Leu-DNR and of β-Ala-Leu-Ala-Leu-DOX in Human Blood Like β-Ala-Leu-Ala-Leu-DNR (SEQ ID NO:1), β-Ala-Leu-Ala-Leu-DOX (SEQ ID NO:2) is stable when incubated at 37 C in human blood. In effect, less than 2% of the prodrug is hydrolyzed to L-Leu-DOX after 2 hours, while the other derivatives synthesized hydrolyze rapidly in the presence of human blood (see Table 1 below).

TABLE 1

HYDROLYSIS OF DAUNORUBICIN (DNR) AND DOXORUBICIN (DOX) DERIVATIVES

| COMPOUND | Human Blood | MCF-7/6 Conditioned Medium | |
|---|---|---|---|
| L-Leu-DNR | + | − | Hydrolysis to DNR |
| D-Leu-DNR | − | − | " |
| diEthyl-β-Ala-DNR | − | − | " |
| L-NorLeu-DNR | − | − | |
| L-Ala-L-Leu-DNR | + | + | Hydrolysis to L-Leu-DNR |
| L-Ala-L-Ala-DNR | + | − | Hydrolysis to DNR |
| L-Ala-L-Ileu-DNR | + | + | " |
| L-Ala-L-NorLeu-DNR | − | − | " |
| β-Ala-L-Leu-DNR | − | − | " |
| L-Phe-L-Leu-DNR | + | (±) | " |
| L-Ala-L-Ala-L-Leu-DNR | + | − | Hydrolysis to L-Leu-DNR |
| L-NLeu-β-L-Ala-L-Leu-DNR | + | + | " |
| L-Leu-L-Ala-L-Leu-DNR | + | + | " |
| L-Ala-L-Leu-L-Ala-L-Leu-DNR (SEQ ID NO: 5) | + | + | " |
| L-Ala-L-Leu-Gly-L-Leu-DNR (SEQ ID NO: 6) | + | (±) | Hydrolysis to DNR |
| Gly-L-Leu-Gly-L-Leu-DNR (SEQ ID NO: 7) | + | + | " |
| Succ-L-Ala-L-Leu-DNR | − | − | Hydrolysis to L-Leu-DNR |
| Succ-L-Leu-L-Ala-L-Leu-DNR | − | − | " |
| Succ-L-Ala-L-Leu-L-Ala-L-Leu-DNR (SEQ ID NO: 8) | (+) | − | " |
| pGlu-L-Ala-L-Leu-L-Ala-L-Leu-DOX (SEQ ID NO: 9) | + | − | Hydrolysis to L-Leu-DOX |
| D-Leu-L-Ala-L-Leu-DNR | − | − | Hydrolysis to L-Leu-DNR |
| D-Ala-L-Leu-L-Ala-L-Leu-DNR (SEQ ID NO: 10) | + | (+) | " |
| D-Leu-L-Ala-L-Leu-L-Ala-L-Leu-DNR (SEQ ID NO: 11) | + | + | " |
| D-Leu-D-Ala-L-Leu-L-Ala-L-Leu-DNR (SEQ ID NO: 12) | (+) | (+) | " |
| β-L-Ala-L-Leu-DNR | − | − | " |
| L-NLeu--L-Ala-L-Leu-DNR | + | + | " |
| β-Ala-L-Ala-L-Leu-DNR | − | − | " |
| β-Ala-L-Leu-L-Ala-L-Leu-DNR (SEQ ID NO: 1) | − | + | Hydrolysis to L-Leu-DNR |
| β-Ala-L-Leu-L-Ala-L-Leu-DOX (SEQ ID NO: 2) | − | + | Hydrolysis to L-Leu-DOX |
| β-Ala-L-Leu-L-Ala-L-Leu-COU* (SEQ ID NO: 13) | − | + | Hydrolysis to L-Leu-COU |

EXAMPLE 5

Figure 4A:
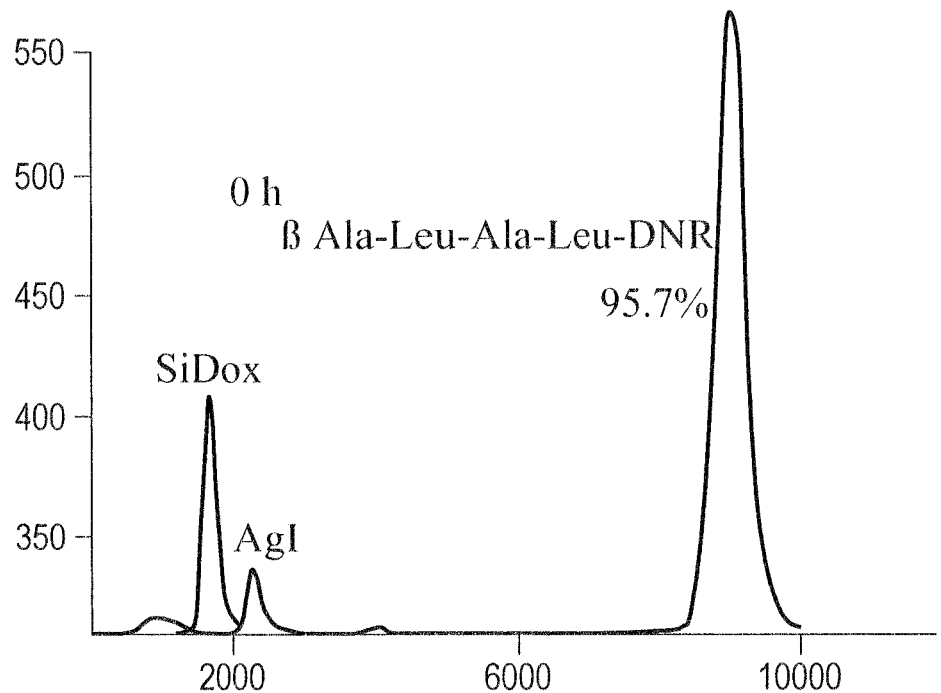
FIG. 4 shows the hydrolysis of β-Ala-Leu-Ala-Leu-daunorubicin (SEQ ID NO:1) in conditioned medium from MCF7/ADR human mammary carcinoma cells (chromatogram at time zero (a) and after one hour of incubation (b)).
Figure 4B:
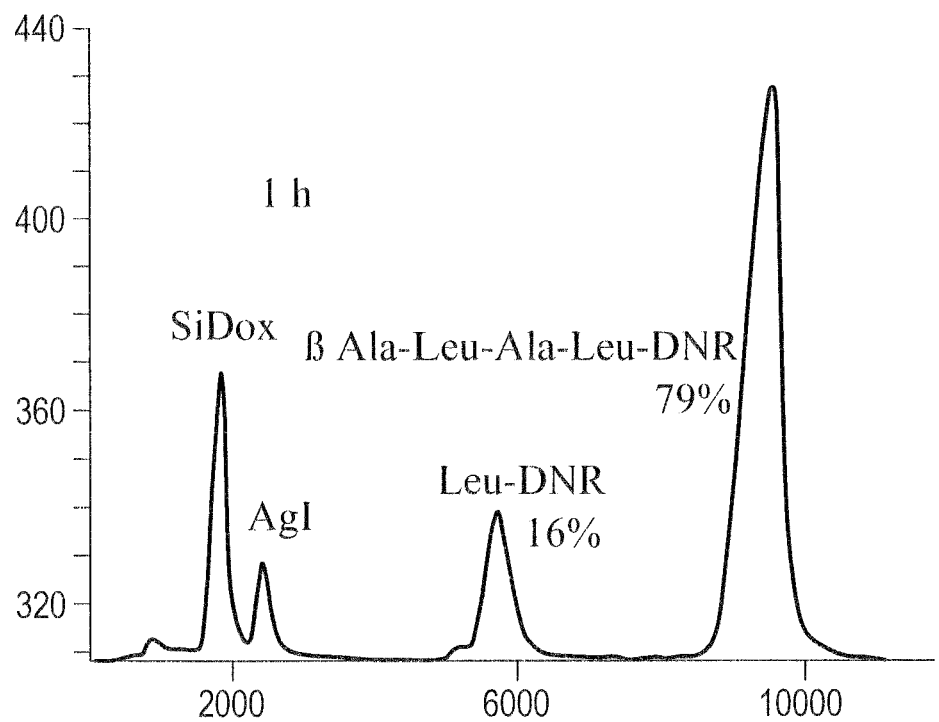

Degradation of β-Ala-Leu-Ala-Leu-DNR in Conditioned Medium from MCF7/ADR Mammary Carcinoma Cells When β-Ala-Leu-Ala-Leu-DNR (SEQ ID NO:1) is incubated at 37 C for 1 hour in conditioned medium from anthracycline-resistant MCF7 cells (MCF7/ADR line), the only metabolite now to be found is L-Leu-DNR (FIG. 4).

Anthracycline-sensitive and -resistant MCF7/6 cells both secrete the protease or proteases capable of hydrolyzing the compound according to the invention.

EXAMPLE 6

Degradation of β-Ala-Leu-Ala-Leu-DNR in Conditioned Medium from HepG2 Hepatocarcinoma Cells When β-Ala-Leu-Ala-Leu-DNR (SEQ ID NO:1) is incubated at 37 C for 2 hours in conditioned medium from HepG2 hepatocarcinoma cells, the main metabolites to be found are L-Leu-DNR (27% of the total fluorescence) and L-Ala-L-Leu-DNR (8%). The percentage of hydrolysis cannot be compared between MCF7 mammary carcinoma and HepG2 hepatocarcinoma cells, since the number of cells from which the conditioned media have been recovered, as well as the concentrations of the conditioned media, are different. The qualitative analysis nevertheless shows that the peptidase or peptidases is/are not specific to MCF7 cells.

EXAMPLE 7

Figure 5A:
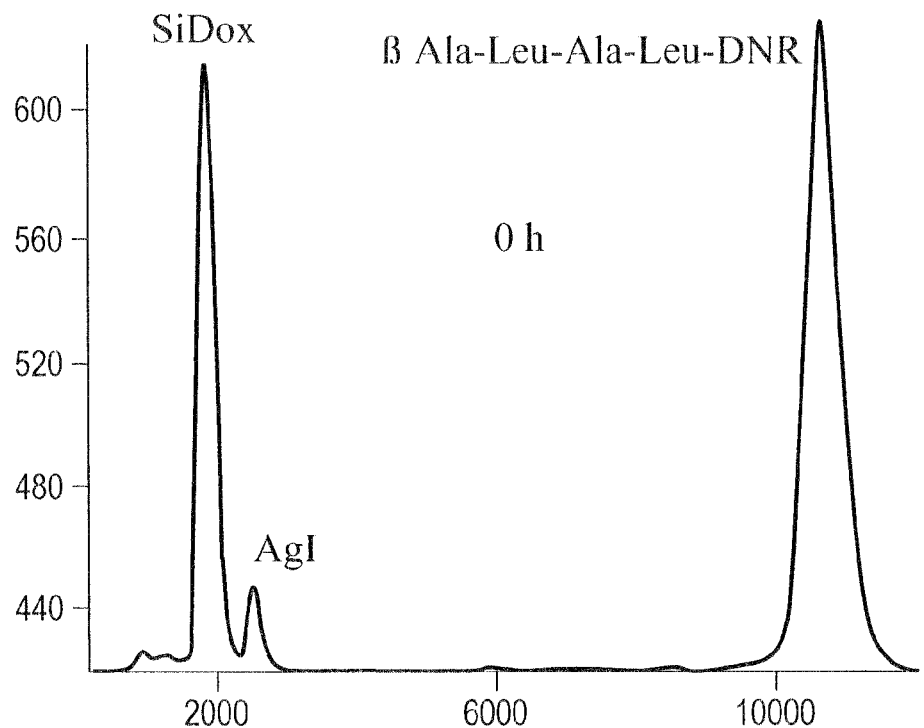
FIG. 5 shows the hydrolysis of β-Ala-Leu-Ala-Leu-daunorubicin (SEQ ID NO:1) in conditioned medium from HT29 colon carcinoma cells (chromatogram at time zero (a) and after two hours of incubation (b)).
Figure 5B:
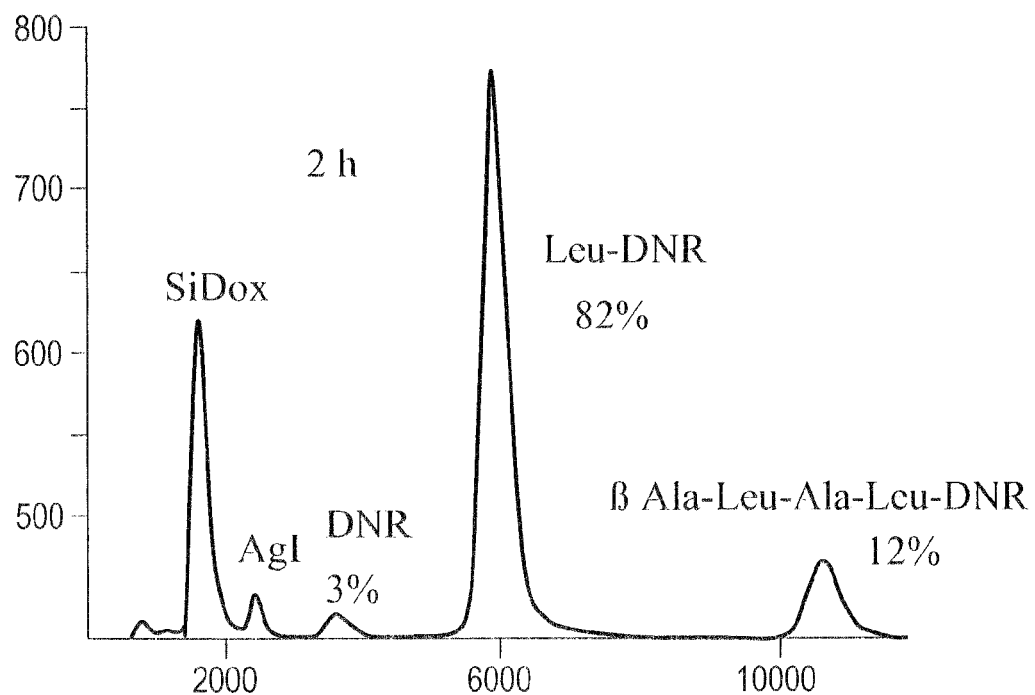

Degradation of β-Ala-Leu-Ala-Leu-DNR in Conditioned Medium from HT29 Colon Carcinoma Cells When β-Ala-Leu-Ala-Leu-DNR (SEQ ID NO:1) is incubated at 37 C for 2 hours in conditioned medium, concentrated 40 times, from HT29 colon carcinoma cells, the main metabolites to be found are L-Leu-DNR (82% of the total fluorescence) and L-Leu-L-Ala-L-Leu-DNR and/or DNR (3%), as illustrated in FIG. 5.

EXAMPLE 8

Accumulation of DNR, of L-Leu-DNR and of β-Ala-L-Leu-L-Ala-L-Leu-DNR in MCF7/6 Tumor Cells MCF7/6 human mammary carcinoma cells were incubated in the presence of β-Ala-Leu-Ala-Leu-DNR (SEQ ID NO:1) at a concentration of 10 μg eq. DNR/ml. After various times, the accumulation of the prodrugs and of their fluorescent metabolites were determined by HPLC after extraction of the products at basic pH according to a method developed in the laboratory. Accumulations, expressed in μg/mg of cellular proteins, were compared with those of DNR and of DOX as well as with those of L-Leu-DNR and L-Leu-DOX. The metabolites were identified by determining the retention times of reference products synthesized in the laboratory.

Figure 6:
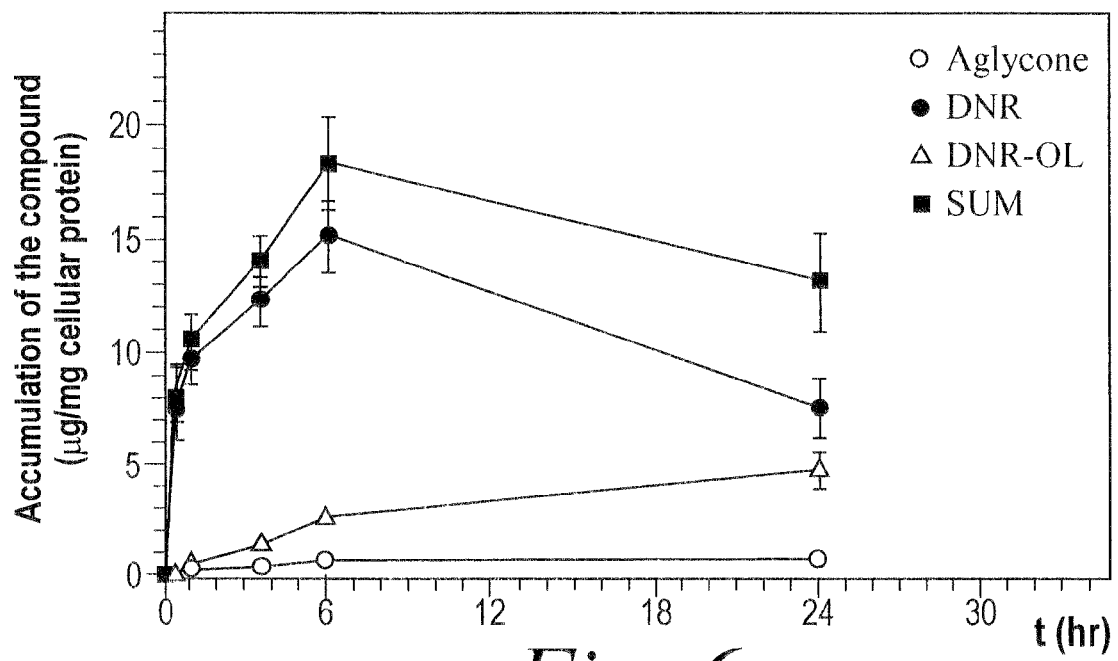
FIG. 6 shows the accumulation of daunorubicin (DNR) at a concentration of 10 μg/ml by confluent MCF7/6 cells.

DNR accumulates rapidly in MCF7/6 cells essentially in unchanged form, the maximum accumulation (±15 μg/mg of cellular proteins) being reached after 6 hours of incubation. The accumulation of DNR decreases thereafter up to 24 hours. The main intracellular metabolite is daunorubicinol, resulting from the reduction of the ketone function of DNR at position C13 by intracellular reductases (FIG. 6).

Figure 7:
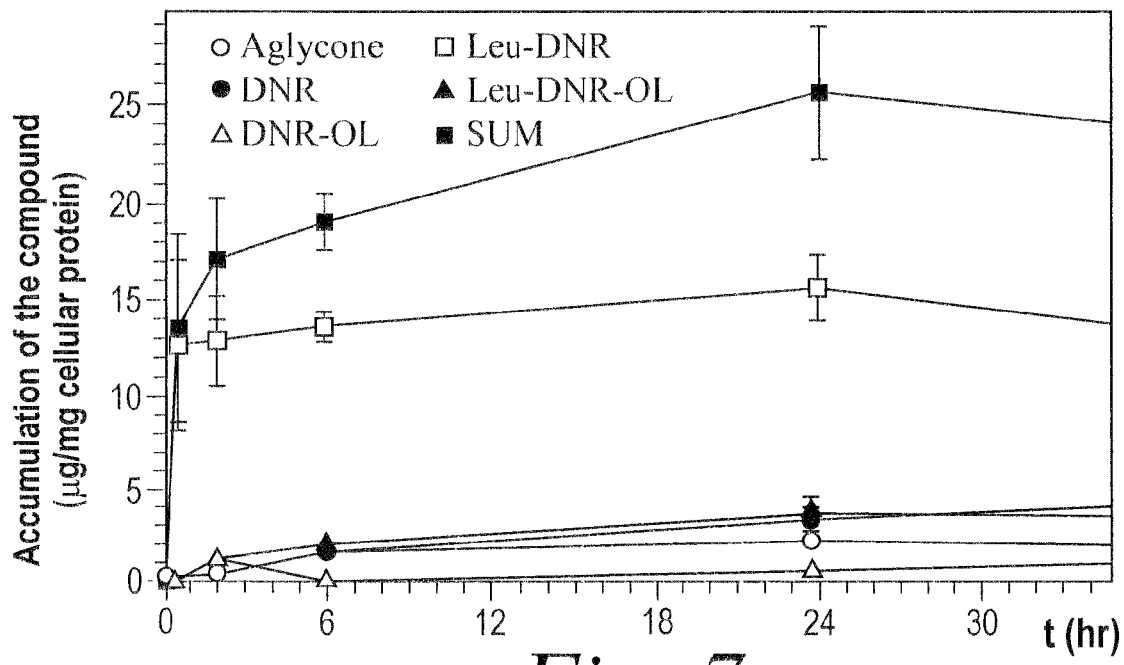
FIG. 7 shows the accumulation of N-L-leucyldaunorubicin (Leu-DNR) at a concentration of 10 μg eq. DNR/ml by confluent MCF7/6 cells.
Figure 8:
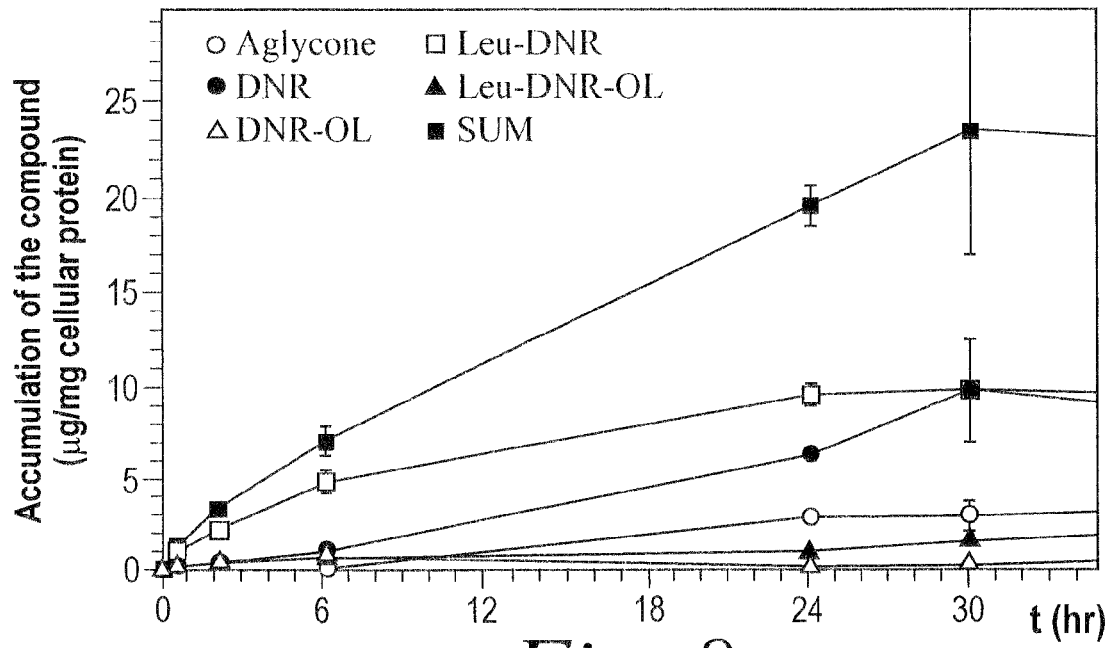
FIG. 8 shows the accumulation of β-Ala-Leu-Ala-Leu-daunorubicin (SEQ ID NO:1) at a concentration of 10 μg eq. DNR/ml by confluent MCF7/6 cells.

L-Leu-DNR is also accumulated very rapidly by MCF7/6 cells, but at lower levels, and the accumulation reaches a plateau after 24 hours of incubation, lying at ±14 μg/mg of cellular proteins. DNR gradually forms intracellularly over time to reach 14% of the total intracellular fluorescence after 24 hours of incubation (FIG. 7).

β-Ala-Leu-Ala-Leu-DNR (SEQ ID NO:1), incubated for 24 hours in the presence of MCF7/6 cells, accumulates in unchanged form much less than DNR and than L-Leu-DNR, the level of accumulation being only ±1 μg/mg of cellular proteins (FIG. 8). L-Leu-DNR, formed extracellularly, and DNR are the species chiefly to be found in the cells after 24 hours of incubation. The DNR to be found intracellularly represents, after 24 hours of incubation, approximately 40% of the total fluorescence.

TABLE 2

Intracellular concentrations of starting material L-Leu-DNR and DNR after 6 hours of incubation of MCF7/6 cells with either DNR, L-Leu-DNR or β-Ala-Leu-Ala-Leu-DNR (SEQ ID NO: 1).

| Incubation with | Starting material (μg/mg cellular | Leu-DNR formed proteins) | DNR formed |
|---|---|---|---|
| DNR | 14.9 | — | — |
| Leu-DNR | 13.4 | — | 1.5 |
| β-Ala-Leu-Ala-Leu-DNR (SEQ ID NO: 1) | 0.3 | 4.5 | 0.9 |

The results in Table 2 show that the passage of peptide derivatives of DNR through cell membranes decreases when the length of the peptide chain increases, and that β-Ala-Leu-Ala-Leu-DNR (SEQ ID NO:1) is a precursor of Leu-DNR, activated extracellularly. The Leu-DNR liberated accumulates intracellularly and itself becomes an intracellular precursor of DNR.

EXAMPLE 9

Accumulation of DNR, of L-Leu-DNR and of β-Ala-Leu-Ala-Leu-DNR in MRC5 Normal Cells MRC5 fibroblast cells were incubated in the presence of β-Ala-Leu-Ala-Leu-DNR (SEQ ID NO:1) at a concentration of 10 μg eq. DNR/ml. At various times, the accumulation of the prodrugs and of their fluorescent metabolites was determined by HPLC after extraction of the products at basic pH according to a method developed in the laboratory. Accumulations, expressed in μg/mg of cellular proteins, were compared with those of DNR and of L-Leu-DNR. The metabolites were identified by determining the retention times of reference products synthesized in the laboratory.

Figure 9:
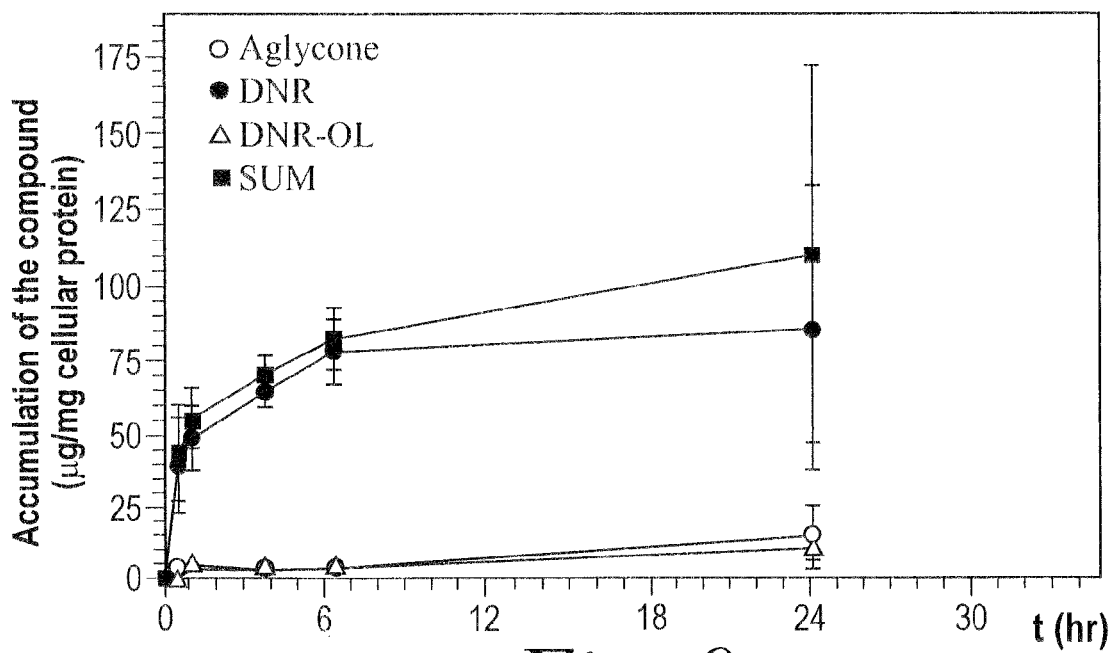
FIG. 9 shows the accumulation of daunorubicin (DNR) at a concentration of 10 μg/ml by confluent MRC5 fibroblast cells.

DNR accumulates mainly in MRC5 cells in unchanged form, and the accumulation reaches a plateau of ±76 μg/mg of cellular proteins after 6 hours, the major metabolite being daunorubicinol (FIG. 9).

Figure 10:
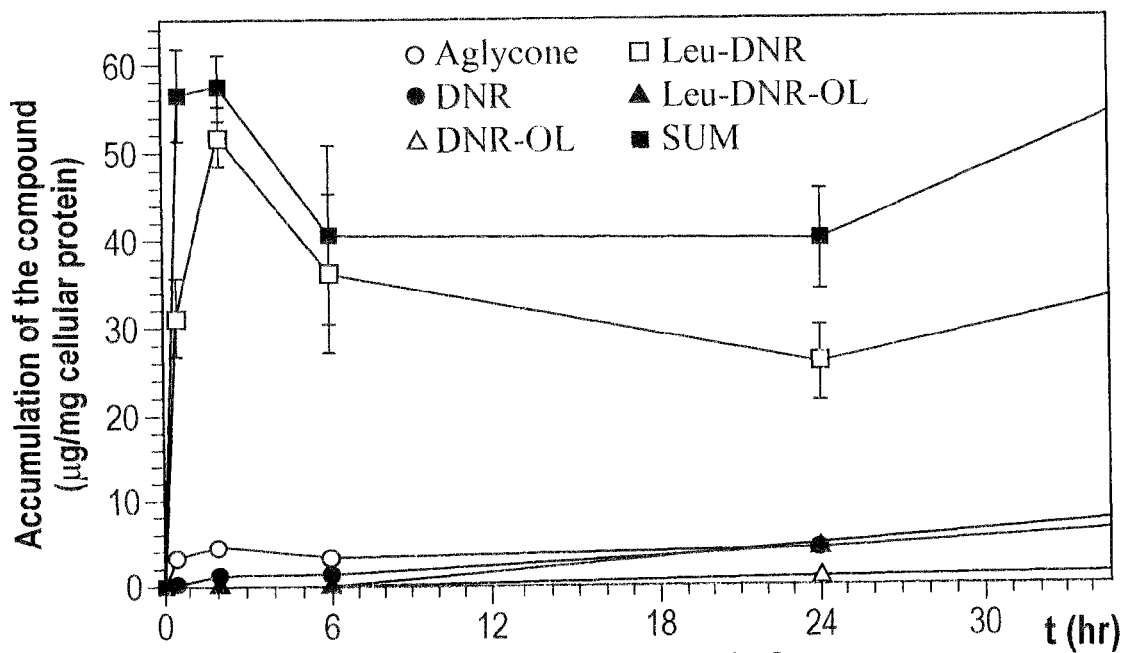
FIG. 10 shows the accumulation of N-L-leucyldaunorubicin (Leu-DNR) at a concentration of 10 μg eq. DNR/ml by confluent MRC5 fibroblast cells.
Figure 11:
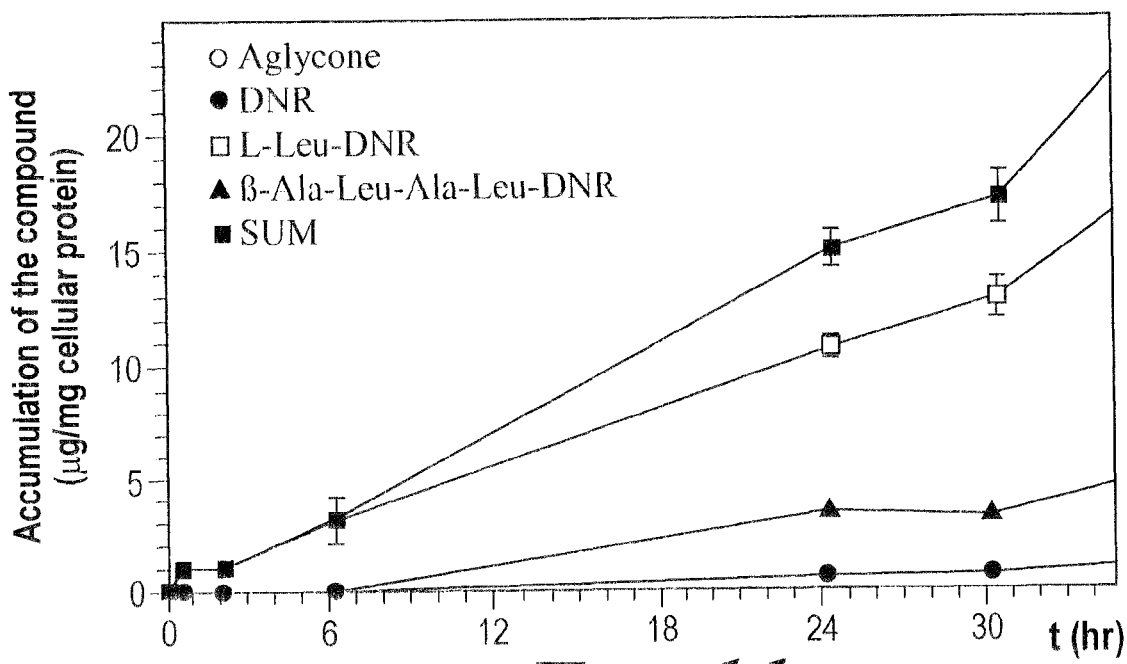
FIG. 11 shows the accumulation of β-Ala-Leu-Ala-Leu-daunorubicin (SEQ ID NO:1) at a concentration of 10 μg eq. DNR/ml by confluent MRC5 fibroblast cells.

L-Leu-DNR is also accumulated very rapidly by MRC5 cells, but at lower levels, and the accumulation reaches a plateau after 24 hours of incubation, lying at ±40 μg/mg of cellular proteins. The main metabolites are DNR as well as L-Leu-DNR-OL (FIG. 10).

β-Ala-Leu-Ala-Leu-DNR (SEQ ID NO:1) incubated for 24 hours in the presence of MRC5 cells, accumulates much less than DNR and then L-Leu-DNR, the level of accumulation being only ±3.3 μg/mg of cellular proteins (FIG. 11). L-Leu-DNR, formed extracellularly, is the species chiefly to be found in the cells. Its accumulation increases linearly up to 24 hours of incubation.

These results corroborate those obtained on MCF7/6 cells, namely that the compound β-Ala-Leu-Ala-Leu-DNR (SEQ ID NO:1) barely enters the cells at all (300 times less than DNR after 6 hours), and that L-Leu-DNR formed extracellularly is the species which chiefly accumulates in MRC5 cells (Table 3).

TABLE 3

Intracellular concentrations of starting material L-Leu-DNR and DNR after 6 hours of incubation of MRC5 cells with either DNR, L-Leu-DNR or β-Ala-Leu-Ala-Leu-DNR (SEQ ID NO: 1).

| Incubation with | Starting material (μg/mg cellular proteins) | Leu-DNR formed | DNR formed |
|---|---|---|---|
| DNR | 77.4 | — | — |
| Leu-DNR | 36.0 | — | 1.3 |
| β-Ala-Leu-Ala-Leu-DNR (SEQ ID NO: 1) | 0.03 | 3.1 | 0.08 |

In the MCF7/6 tumor line, the intracellular levels of DNR obtained after 24 hours of incubation in the presence of the compound β-Ala-Leu-Ala-Leu-DNR (SEQ ID NO:1) are 12 times as high as in MRC5 fibroblasts.

When the cells are incubated in the presence of Leu-DNR and of DNR, the ratio of the intracellular DNR levels is only 0.37 and 0.19, respectively.

EXAMPLE 10

Cytotoxicity of β-Ala-Leu-Ala-Leu-DNR with Respect to MCF7/6 Tumor Cells and MRC5 Normal Cells The cytotoxicity of the DNR prodrug, of Leu-DNR and of DNR was compared on MCF7/6 and MRC5 cells maintained in growth for 72 hours in the presence of the various compounds.

The cytotoxicities of β-Ala-Leu-Ala-Leu-DNR (SEQ ID NO:1) of L-Leu-DNR and of DNR were determined on MCF7/6 cells growing in 96-well dishes, incubated in the presence of increasing concentrations of the various compounds. After 72 hours, the cells are incubated for 48 hours in the absence of anthracycline, and the cytotoxicity is determined by measuring the cellular proteins by Bradford's technique. A series of 9 concentrations are used, ranging from 700 μg/ml to 0.0035 μg/ml, and each measurement represents a mean and standard deviation of 6 values. The experimental points are adjusted to a sigmoid curve which enables the point of inflection, corresponding to the dose at which half of the cells survive ($IC_{50}$), to be calculated.

Figure 12:
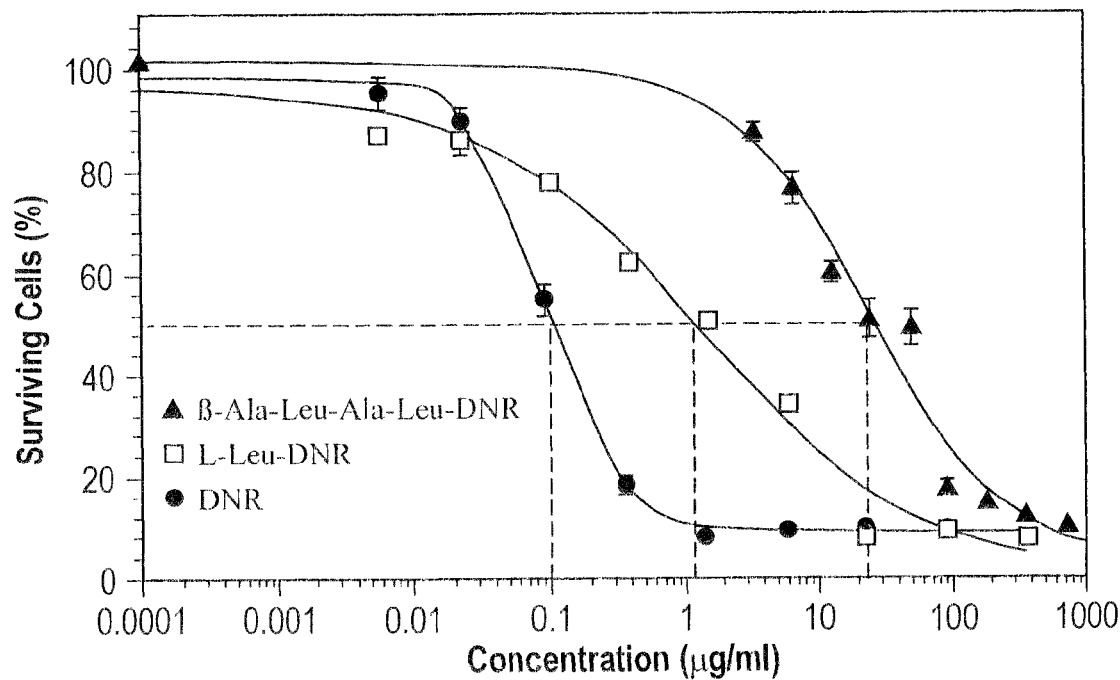
FIG. 12 shows the cytotoxicity of daunorubicin (DNR), L-Leu-daunorubicin and β-Ala-Leu-Ala-Leu-daunorubicin (SEQ ID NO:1) with respect to MCF7/6 cells maintained in growth for 72 hours in the presence of the anthracyclines.

FIG. 12 illustrates that the $IC_{50}$ of DNR is 0.090±0.004 μg/ml. For cells incubated for 72 hours in the presence of L-Leu-DNR, the IC50 is 1.30±0.56 μg/ml. In the case of β-Ala-Leu-Ala-Leu-DNR (SEQ ID NO:1), the IC50 is 22.00±7.31 μg/ml.

Leu-DNR and β-Ala-Leu-Ala-Leu-DNR (SEQ ID NO:1) are hence 14 times and 244 times, respectively, less cytotoxic than DNR for MCF7/6 human mammary carcinoma cells maintained in growth for 72 hours in the presence of the anthracyclines.

The cytotoxicities of β-Ala-Leu-Ala-Leu-DNR (SEQ ID NO:1) of L-Leu-DNR and of DNR were determined on MRC5 cells growing in 96-well dishes, incubated in the presence of increasing concentrations of the various compounds. After 72 hours, the cells are incubated for 48 hours in the absence of anthracycline, and the cytotoxicity is determined by measuring the cellular proteins by Bradford's technique. A series of 9 concentrations are used, ranging from 700 μg/ml to 0.0035 μg/ml, and each measurement represents a mean and standard deviation of 6 values. The experimental points are adjusted to a sigmoid curve which enables the point of inflection, corresponding to the dose at which half of the cells survive ($IC_{50}$), to be calculated.

Figure 13:
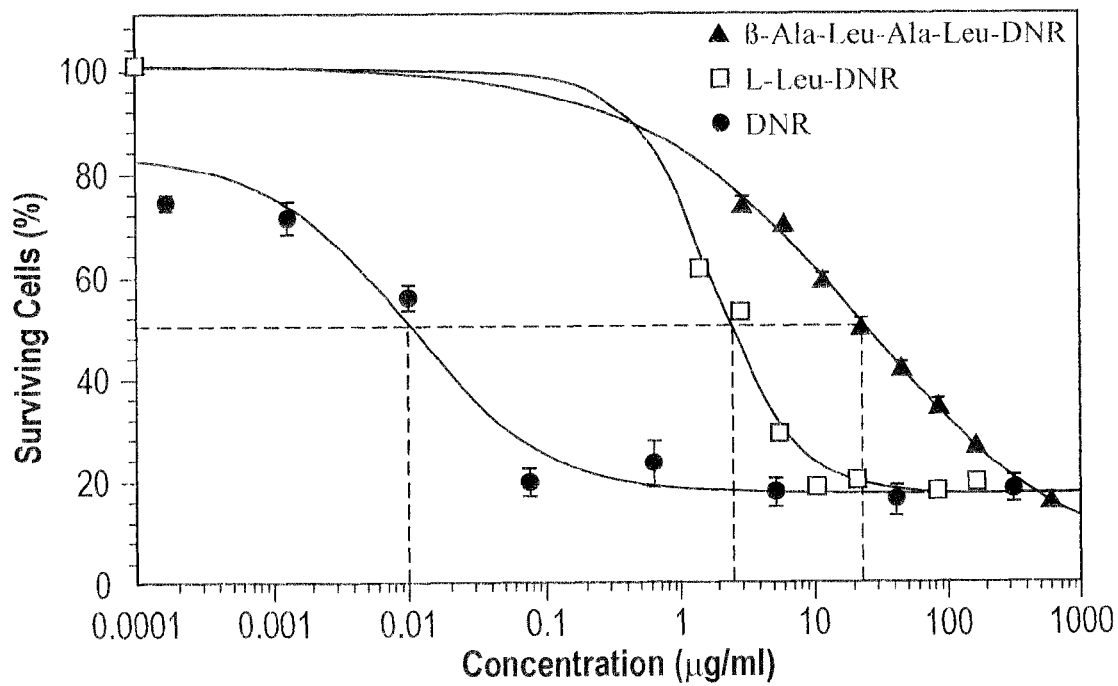
FIG. 13 shows the cytotoxicity of daunorubicin (DNR), L-Leu-daunorubicin and β-Ala-Leu-Ala-Leu-daunorubicin (SEQ ID NO:1) with respect to MRC5 fibroblast cells maintained in growth for 72 hours in the presence of the anthracyclines.

FIG. 13 illustrates that the $IC_{50}$ of DNR is 0.010±0.006 μg/ml. For cells incubated for 72 hours in the presence of L-Leu-DNR, the $IC_{50}$ is 1.78±0.23 μg/ml. In the case of β-Ala-Leu-Ala-Leu-DNR (SEQ ID NO:1), the $IC_{50}$ is 23.14±4.81 μg/ml.

Leu-DNR and β-Ala-Leu-Ala-Leu-DNR (SEQ ID NO:1) are hence 172 times and 2230 times, respectively, less cytotoxic than DNR for MRC5 fibroblast cells maintained in growth for 72 hours in the presence of the anthracyclines.

Both for the tumor cells and for the fibroblast cells, the DNR precursor is much less toxic than the parent compound. It remains to be determined whether this decrease in toxicity observed in vitro is also observed in vivo.

EXAMPLE 11

In Vivo Acute Toxicity

The toxicity of β-Ala-Leu-Ala-Leu-DNR (SEQ ID NO:1) was compared with that of daunorubicin on mice. In the in vivo study of the acute toxicity of a medicinal product, determination of the median lethal dose (lethal dose for 50% of the animals or LD50) occupies an important place. In spite of the fact that it does not represent a biological constant, it gives information regarding the acute toxicity of the product injected. The $LD_{50}$ is a simple test in which increasing amounts of the test product are administered intravenously (i.v.) in a single injection and intraperitoneally (i.p.) in 5 injections, one injection daily for 5 consecutive days. The mortality of the animals is monitored as a function of time. At the end of the observation period, usually 30 days, the value of the $LD_{50}$ is obtained by linear regression of the percentage mortality (on a probit scale) as a function of the logarithm of the dose administered (O. K. Chan and A. W. Hayes, *Principles and methods for acute toxicity and eye irritancy*, in Principles and methods of toxicology, Second edition. Ed. by A. W. Hayes, Raven Press, New York, USA (1989), pp. 169-220; D. Deprez-De Campeneere and A. Trouet. *DNA-Anthracycline Complexes. I. Toxicity in mice and chemotherapeutic activity against L1210 Leukaemia off Daunorubicin-DNA and Adriamycin-DNA*, Eur. J. Cancer, 16 (1980), pp. 981-986; H. E. Skipper, L. H. Schmidt, A. Goldin and J. M. Venditti. *A manual on quantitative drug evaluation in experimental tumor systems*, Cancer Chemother. Rep. 17 (1.962), pp. 1-178).

In the case where the Lb50 is not reached, the daily weight changes of the mice also gives information regarding the acute toxicity of the products administered.

1. Materials and Methods.

The acute toxicity of these two drugs was studied via the i.v. and i.p. routes on a single strain of mouse. Female NMRI mice (nonconsanguineous SPF-Han, approximately 5 weeks old and of mean weight 14.6 grams, supplied by IFFA-CREDO Belgium) remained in quarantine for one week. On the day before injection, they were distributed in groups of 5 (β-Ala-Leu-Ala-Leu-DNR (SEQ ID NO:1)) and 7 (DNR) per dose to be injected; their weight was noted again (approximately 22 grams on average).

Injections were performed systematically in the morning (single injection into the caudal vein for the i.v. route and injections on 5 consecutive days into the peritoneum for the i.p. route), using 1.0 ml syringes and sterile 30 G (i.v.) and 27 G (i.p) needles. All handling of animals was performed with gloves, and maintenance of the animals was performed systematically every week.

β-Ala-Leu-Ala-Leu-DNR (SEQ ID NO:1) was injected i.v. at doses of 30, 60 and 120 mg/kg and i.p. at total doses of 10, 15, 20, 25, 30, 45 and 60 mg/kg. On two additional groups, β-Ala-Leu-Ala-Leu-DNR (SEQ ID NO:1) was reinjected i.v. at total doses of 30 and 60 mg/kg in one and two, respectively, consecutive injections at 30 mg/kg.

DNR was injected i.v. at doses of 10, 15, 20, 25, 30 and 35 mg/kg and i.p. at doses of 2.0; 2.5; 3.0 and 3.5 mg/kg.

Solutions of β-Ala-Leu-Ala-Leu-DNR (SEQ ID NO:1) and of DNR were prepared in physiological NaCl in such a way that the injected volume would correspond to 0.1 ml per 10 grams mouse body weight. The concentrations of the solutions were verified by spectrophotometry.

From the day of injection (DO) onwards, the mice were monitored clinically, with a daily record of dead mice. The weight of the mice was measured almost every day. The observation period was extended beyond one month so that the signs of late toxicity could be spotted more readily. At the end of the study, the surviving mice were sacrificed, according to the standards pertaining to animal experiments (D. B. McGregor. *Ethics in experiments on animals*, in Experiments in toxicology, First edition. Ed. by D. Anderson and D. M. Conning. The Royal Society of Chemistry and The Universities Press. Belfast, Ireland (1988), pp. 512-522).

2. Results.

Toxicity Via the Intraperitoneal Route.

Figure 14:
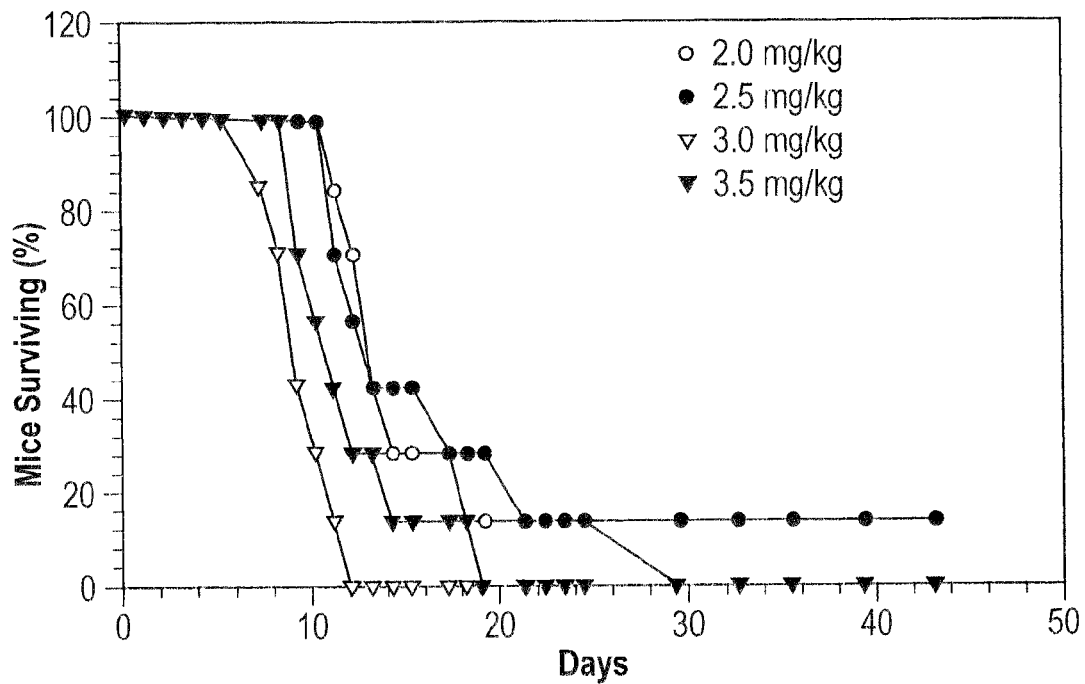
FIG. 14 shows the mortality of female NMRI mice after i.p. administration on 5 consecutive days of daunorubicin (DNR) at total doses of between 2.0 and 3.5 mg/kg.

As illustrated in FIG. 14, as regards DNR, a considerable toxicity is observed as a function of the concentration, which toxicity manifests itself in mortality of the mice, from day 7 at a dose of 3.5 mg/kg (1 mouse dead out of 7), from day 9 at a dose of 3.0 mg/kg (2 mice dead out of 7) and from day 11 at doses of 2.5 and 2.0 mg/kg (2 mice and 1 mouse, respectively, dead out of 7).

There is no mouse surviving on day 12 (dose of 3.5 mg/kg, on day 19 (dose of 3.0 mg/kg) and on day 29 (dose of 2.0 mg/kg). The only mouse surviving on day 43 is one of those injected at a dose of 2.5 mg/kg. These results confirm those described previously (D. Deprez-De Campeneere and A. Trouet. *DNA-Anthracycline Complexes. I. Toxicity in mice and chemotherapeutic activity against L1210 Leukaemia of Daunorubicin-DNA and Adriamycin-DNA*, Eur. J. Cancer, 16 (1980), pp. 981-986).

Figure 15:
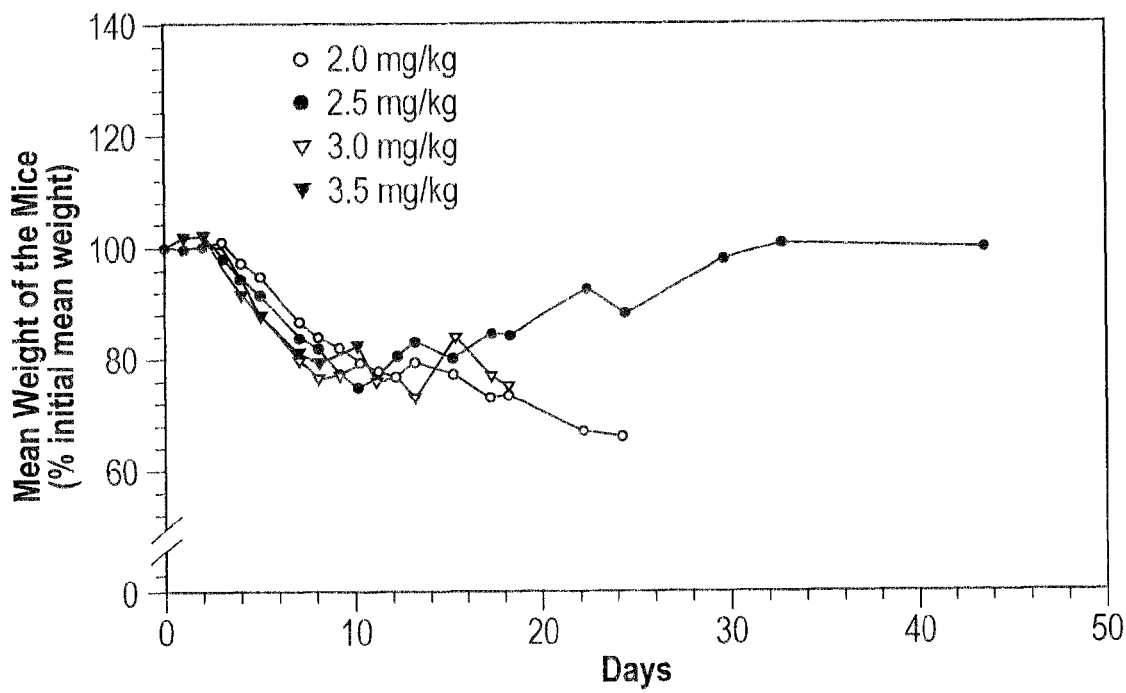
FIG. 15 shows the changes in the mean weight of female NMRI mice which received i.p. on 5 consecutive days total doses of daunorubicin of between 2.0 and 3.5 mg/kg. Weights are expressed as a percentage of the mean initial weight for each group.

FIG. 15 shows that, irrespective of the dose administered, the mice exhibit a weight loss which reaches 30% of the initial weight. This weight loss is generally irreversible, except for one mouse treated at 2.5 mg/kg, which has recovered its initial weight on day 30.

Figure 16:
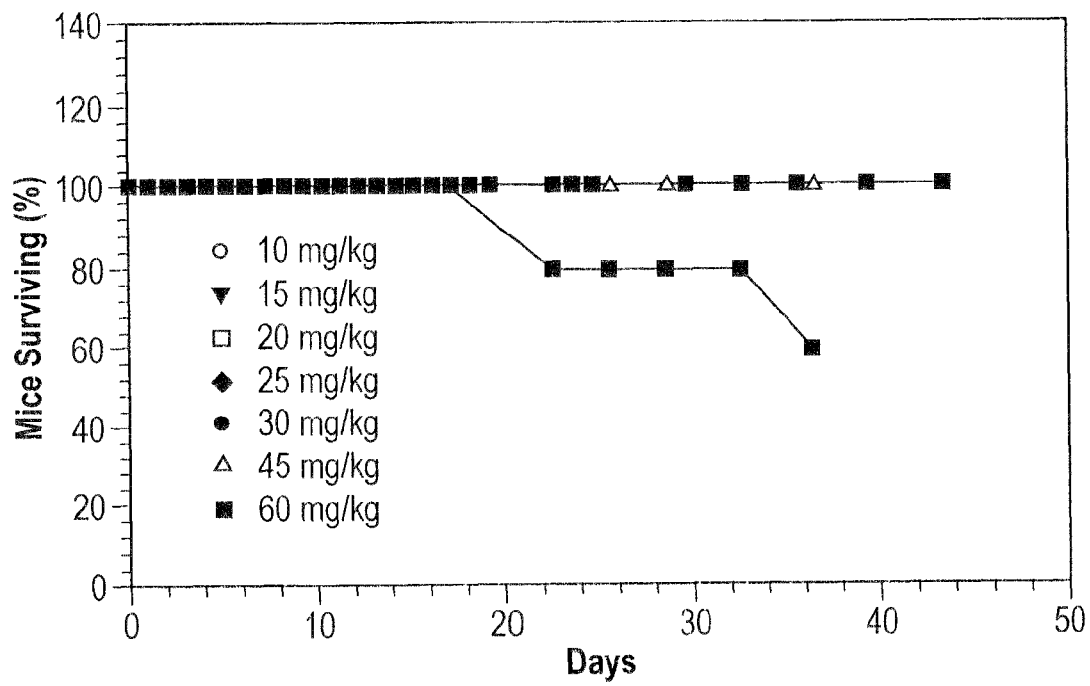
FIG. 16 shows the mortality of female NMRI mice after i.p. administration on 5 consecutive days of β-Ala-Leu-Ala-Leu-daunorubicin (SEQ ID NO:1) at total doses of between 10 and 60 mg/kg.

When β-Ala-Leu-Ala-Leu-DNR (SEQ ID NO:1) is administered i.p. for 5 consecutive days at total doses of between 10 and 45 mg/kg, no mortality is observed, at a dose of 60 mg/kg, 2 mice die on day 22 and a third on day 35 (FIG. 16).

Figure 17:
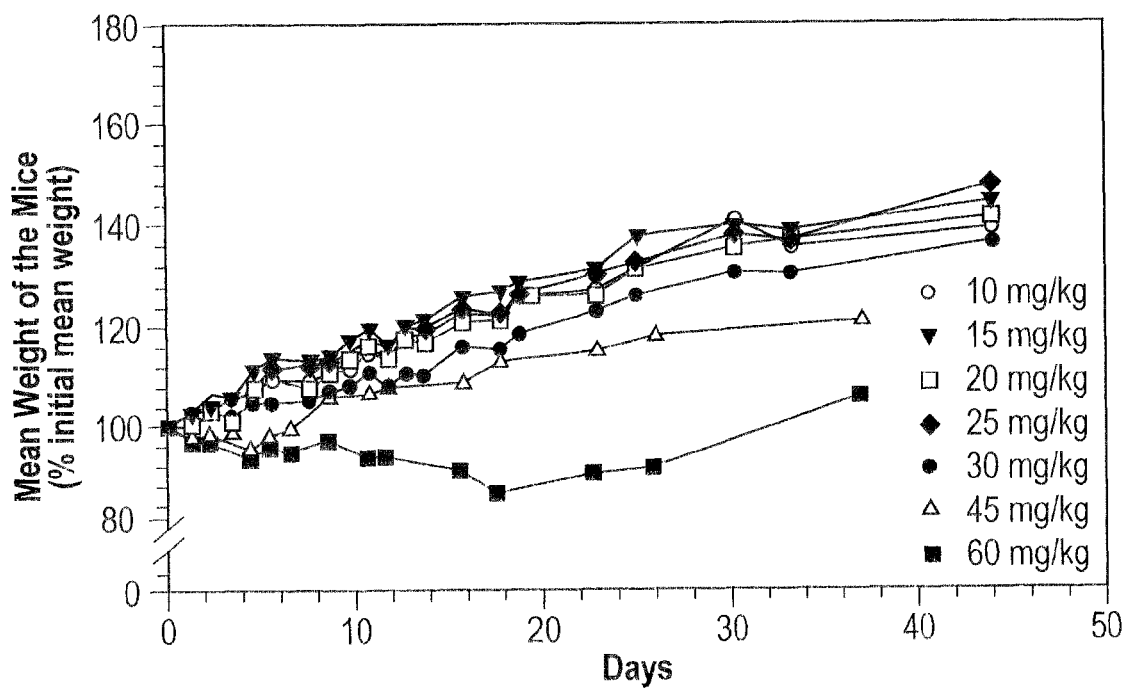
FIG. 17 shows the changes in the mean weight of female NMRI mice which received i.p. on 5 consecutive days total doses of β-Ala-Leu-Ala-Leu-daunorubicin (SEQ ID NO:1) of between 10 and 60 mg/kg. Weights are expressed as a percentage of the mean initial weight for each group.

At total doses of between 10 and 45 mg/kg, no weight loss is observed but, rather, a weight gain of +40% in 40 days (FIG. 17). Analysis of the weight curves does not demonstrate any significant difference. In contrast, at a dose of 45 mg/kg, the mean weight of the mice is stable for the first 7 days, and the increase in weight then reaches only 20% over the next 30 days. At a total dose of 60 mg/kg, the mean weight of the mice decreases by ±15% in 15 days. The two surviving mice recover their initial weight only on day 36 (FIG. 17).

These data show that the dose of 60 mg/kg of β-Ala-Leu-Ala-Leu-DNR (SEQ ID NO:1) is close to the LD50, and hence that β-Ala-Leu-Ala-Leu-DNR (SEQ ID NO:1) is at least 30 times less toxic than DNR in terms of acute toxicity after i.p. administration on 5 consecutive days.

Toxicity Via the Intravenous Route.

Figure 18:
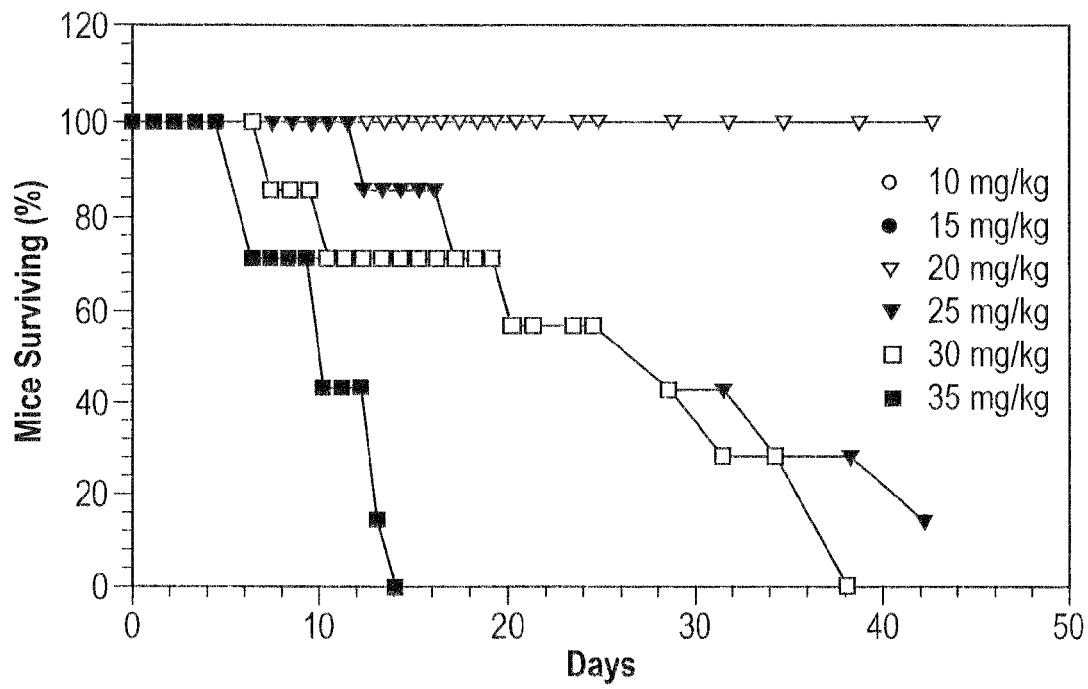
FIG. 18 shows the mortality of female NMRI mice after single i.v. administration of daunorubicin (DNR) at doses of between 10 and 35 mg/kg.

As illustrated in FIG. 18, as regards DNR given i.v. in a single administration to female NMRI mice, no mortality is observed at low doses (10, 15 and 20 mg/kg). At 25 mg/kg, 6 mice die on days 12, 17, 20, 28, 34 and 42, respectively. At higher concentrations of DNR, mortality begins on day 7 (1 mouse out of 7 at a dose of 30 mg/kg) and on day 6 (2 mice out of 7 at a dose of 35 mg/kg). These results accord with those described previously (D. Deprez-De Campeneere and A. Trouet. *DNA-Anthracycline Complexes. I. Toxicity in mice and chemotherapeutic activity against L1210 Leukaemia of Daunorubicin-DNA and Adriamycin-DNA*, Eur. J. Cancer, 16 (1980), pp. 981-986).

Figure 19:
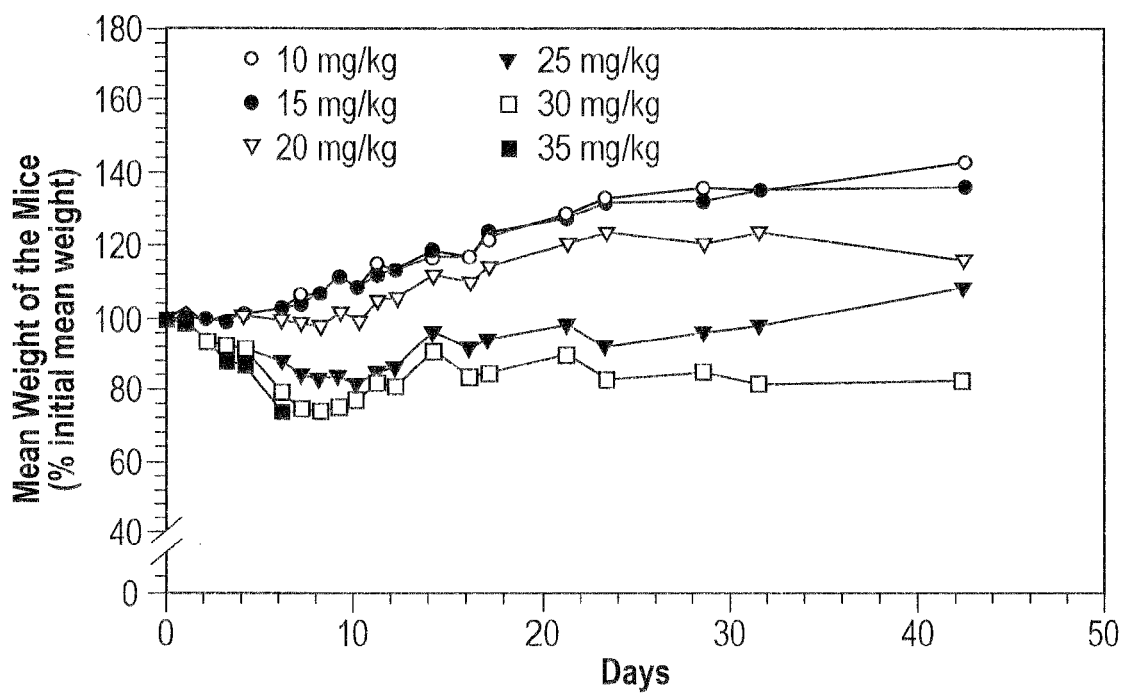
FIG. 19 shows the changes in the mean weight of female NMRI mice which received i.v. doses of daunorubicin (DNR) of between 10 and 35 mg/kg. Weights are expressed as a percentage of the mean initial weight for each group.

The results in FIG. 19 show that the mean weight loss is maximal on day 7 and increases as the dose administered rises. The mice surviving at doses of 30 and 35 mg/kg do not recover their initial weight 30 days after the i.v. injection of DNR.

Figure 20:
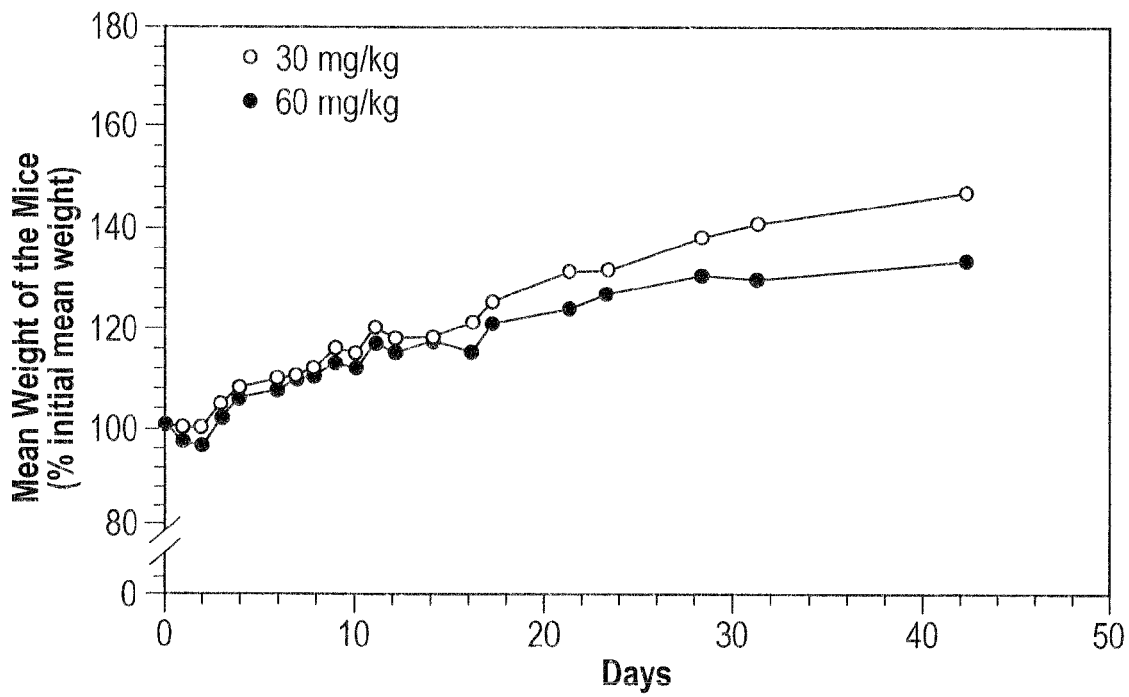
FIG. 20 shows the changes in the mean weight of female NMRI mice which received i.v. doses of β-Ala-Leu-Ala-Leu-daunorubicin (SEQ ID NO:1) of between 30 and 60 mg/kg. Weights are expressed as a percentage of the mean initial weight for each group.

When β-Ala-Leu-Ala-Leu-DNR (SEQ ID NO:1) is administered i.v. at a dose of 30 mg/kg, no mortality is observed, and the mean weight of the mice increases by ±40% in 40 days (FIG. 20). The mean weight of the mice at the end of the experiment is similar to that observed at the same dose of β-Ala-Leu-Ala-Leu-DNR (SEQ ID NO:1) administered i.p. In contrast, at a dose of 60 g/kg, 2 mice die within 5 minutes after injection. This mortality may be due to a hypervolemia following injection of the product much too rapidly. The 3 surviving mice, after a slight weight loss up to day 2, recover their initial weight and then increase in weight (±30% in 40 days). At a dose of 120 mg/kg, the 5 mice die within the 7 minutes following injection, with clinical signs of toxicity.

Figure 21:
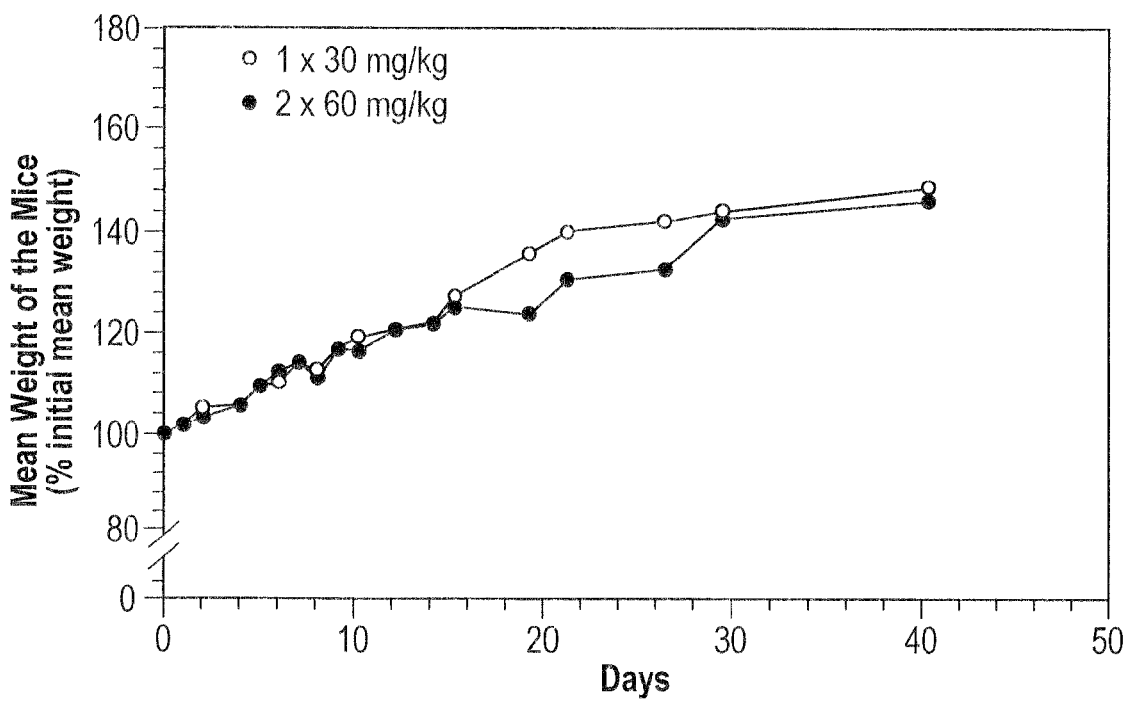
FIG. 21 shows the changes in the mean weight of female NMRI mice which received i.v. either one dose of 30 mg/kg of β-Ala-Leu-Ala-Leu-daunorubicin (SEQ ID NO:1), or two doses of 30 mg/kg each on two consecutive days. Weights are expressed as a percentage of the mean initial weight for each group.

When β-Ala-Leu-Ala-Leu-DNR (SEQ ID NO:1) is administered i.v. at a total dose of 60 mg/kg divided into two i.v. injections of 30 mg/kg each on two consecutive days, no mortality is observed. There is no difference in the changes in the mean weight of the mice which have received one times 30 mg/kg and those which have received 2 times 30 mg/kg of β-Ala-Leu-Ala-Leu-DNR (SEQ ID NO:1) (FIG. 21).

3. Conclusions.

The results obtained enable the conclusion to be drawn that, both via the intravenous route and via the intraperitoneal route, β-Ala-Leu-Ala-Leu-DNR (SEQ ID NO:1) has a much lower acute toxicity than that of DNR, in terms of lethality. These results confirm the reduction in toxicity of the derivative β-Ala-Leu-Ala-Leu-DNR (SEQ ID NO:1).

Experiments identical to those described above were carried out with doxorubicin derivatives.

EXAMPLE 12

Accumulation of DOX, of L-Leu-DOX and of β-Ala-Leu-Ala-Leu-DOX in MCF7/6 Tumor Cells and MRC5 Nontumor Cells MCF7/6 human mammary carcinoma cells and MRC5 human fibroblast line cells were incubated in the presence of β-Ala-Leu-Ala-Leu-DOX (SEQ ID NO:2) at a concentration of 10 µg eq. DOX/ml. After various times, the accumulation of the prodrugs and of their fluorescent metabolites was determined by HPLC after extraction of the products at basic pH according to a method developed in the laboratory. Accumulations, expressed in µg/mg of cellular proteins, were compared with those of DOX and of L-Leu-DOX. The metabolites were identified by determining the retention times of reference products synthesized in the laboratory.

Figure 23:
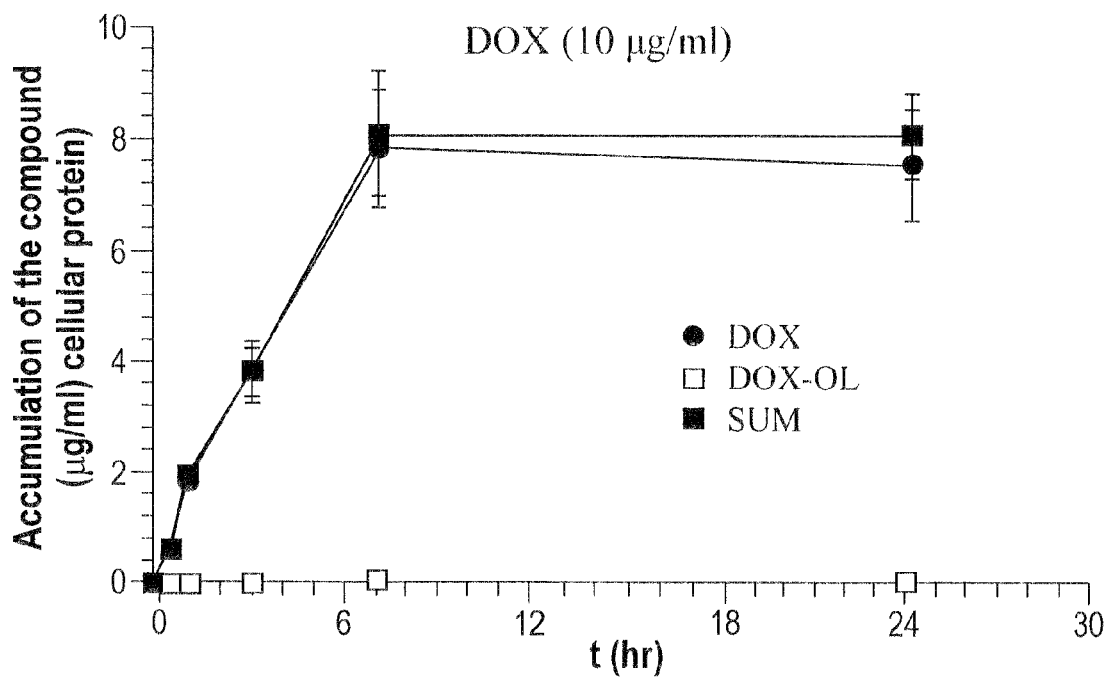
FIG. 23 shows the accumulation of doxorubicin (DOX) at a concentration of 10 μg/ml by confluent MCF7/6 cells.

DOX accumulates mainly in MCF7/6 cells essentially in unchanged form and, after 6 hours, an intracellular level of 6.9 µg/mg of cellular proteins is reached (FIG. 23).

|  | Accumulation after 6 h (µg/mg cellular prot.) | | | IC50 (µg/ml) |
| --- | --- | --- | --- | --- |
|  | A-L-A-L-DOX | Leu-DOX | DOX | (72 h) |
| MCF7/6 DOX | — | — | 6.90 | 0.0025 |
| Leu-DOX | — | 1.10 | 0.25 | 0.02 |
| A-L-A-L-DOX | 0.10 | 0.65 | 0.22 | 3.0 |
| MRC5 DOX | — | — | 11.20 | 0.018 |
| Leu-DOX | — | 1.40 | 0.30 | 0.3 |
| A-L-A-L-DOX | 0.10 | 0.10 | 0.01 | 120 |

Figure 24:
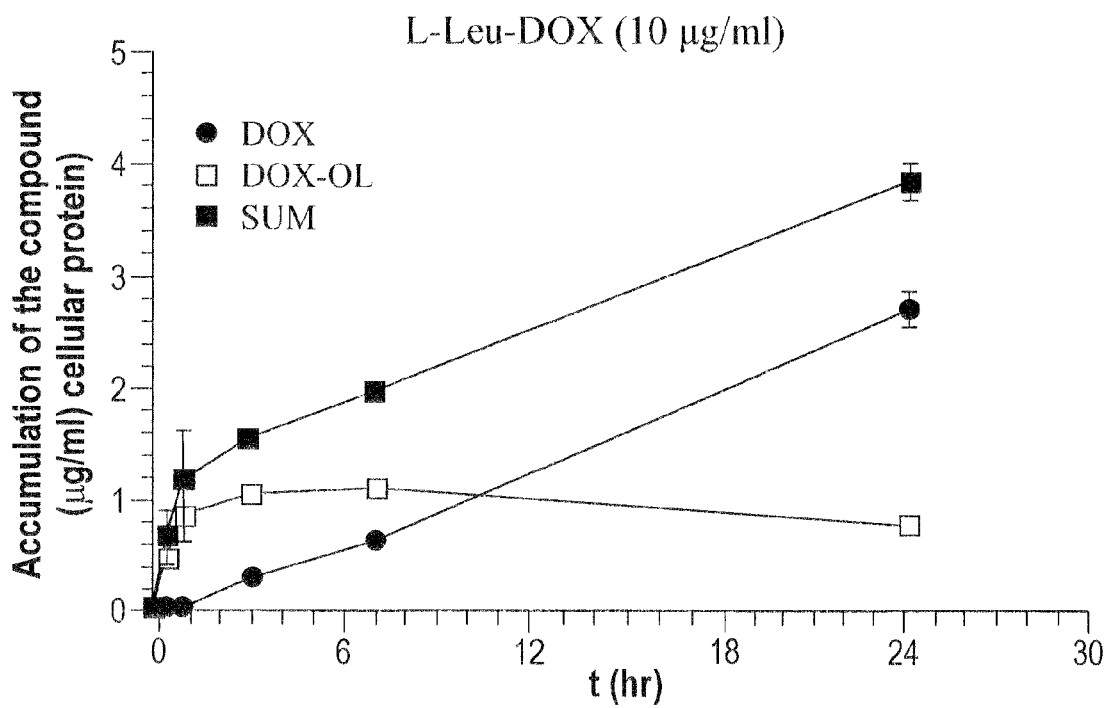
FIG. 24 shows the accumulation of L-Leu-doxorubicin at a concentration of 10 μg/ml by confluent MCF7/6 cells.
Figure 25:
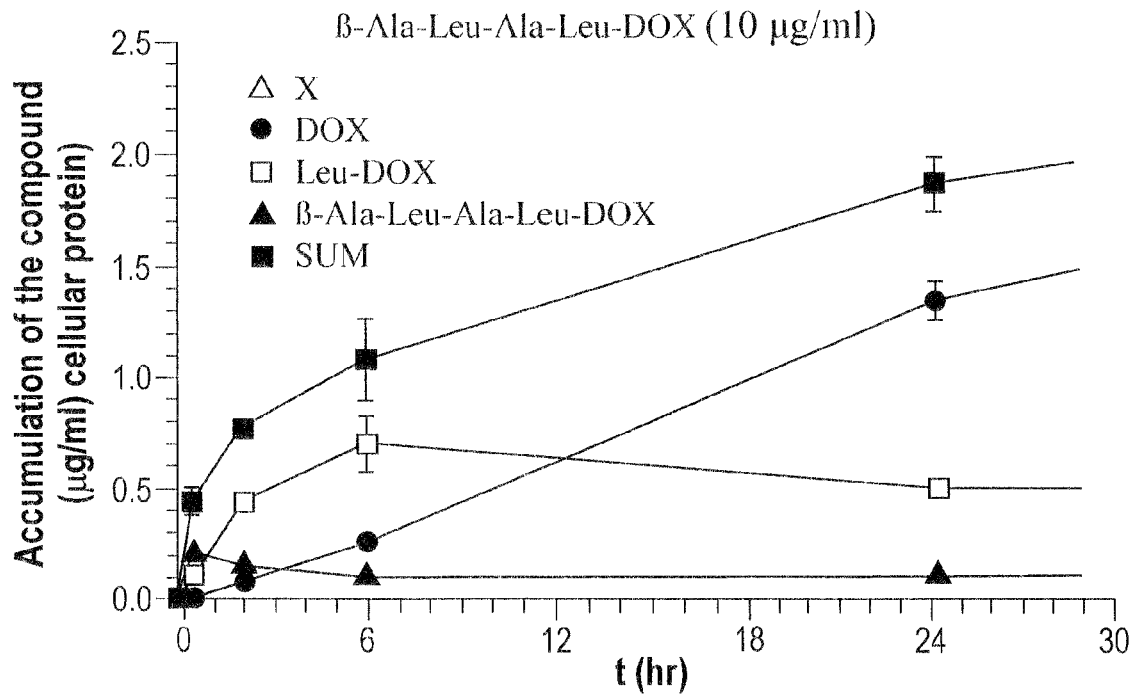
FIG. 25 shows the accumulation of β-Ala-Leu-Ala-Leu-doxorubicin (SEQ ID NO:2) at a concentration of 10 μg/ml by confluent MCF7/6 cells.

Leu-DOX and β-Ala-Leu-Ala-Leu-DOX (SEQ ID NO:2) accumulate 6 times and 69 times, respectively, less than DOX after 6 hours. Intracellularly, the DOX levels are 31 times lower after incubation of the cells in the presence of β-Ala-Leu-Ala-Leu-DOX (SEQ ID NO:2) (FIGS. 24 and 25).

Figure 26:
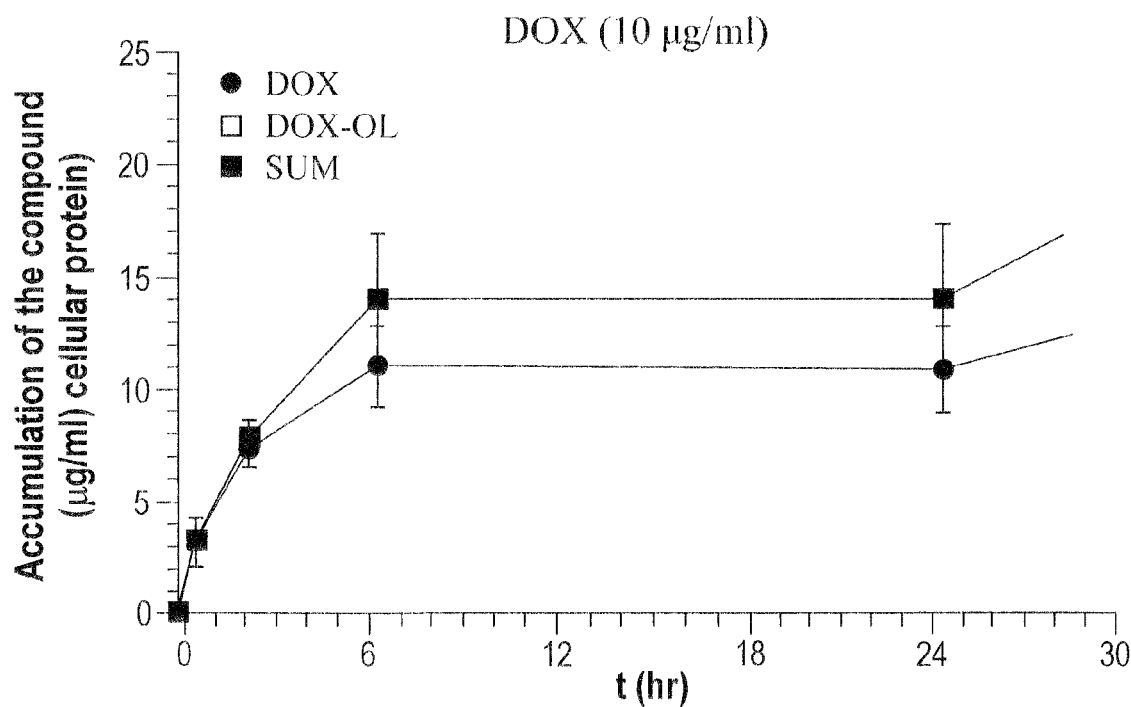
FIG. 26 shows the accumulation of doxorubicin (DOX) at a concentration of 10 μg/ml by confluent MRC5 fibroblast cells.

In MRC5 fibroblast cells incubated for 6 hours in the presence of the anthracyclines at a concentration of 10 µg eq. DOX/ml, DOX accumulates essentially in unchanged form and the accumulation reaches a level of ±11.2 µg/mg of cellular proteins after 6 hours (FIG. 26).

Figure 27:
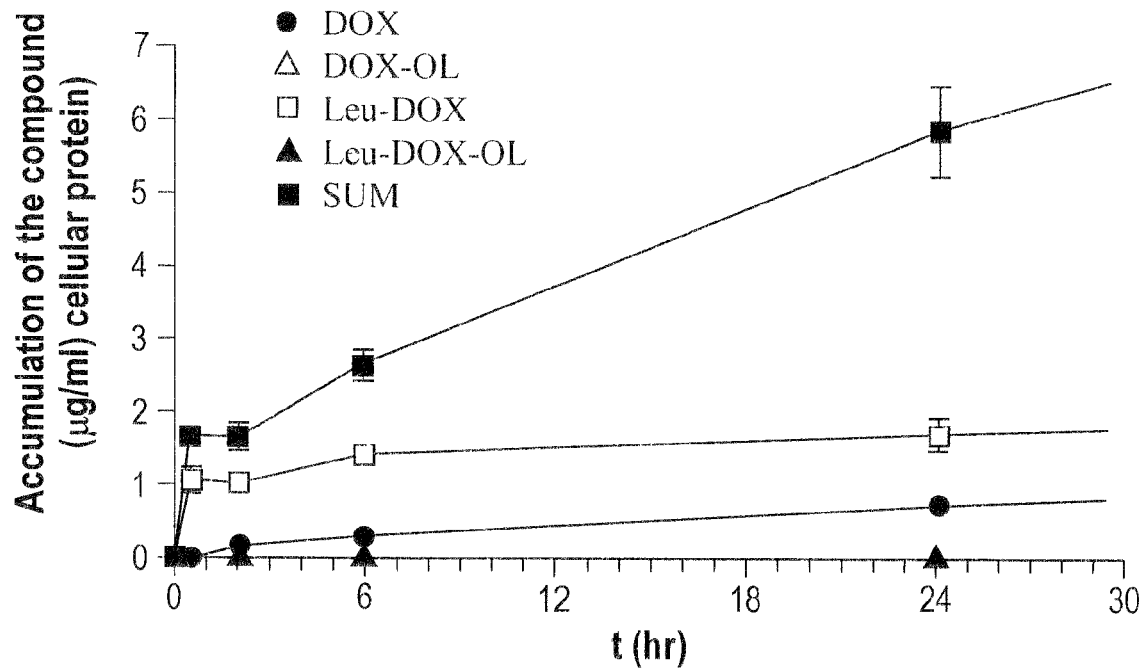
FIG. 27 shows the accumulation of L-Leu-doxorubicin at a concentration of 10 μg/ml by confluent MRC5 fibroblast cells.
Figure 28:
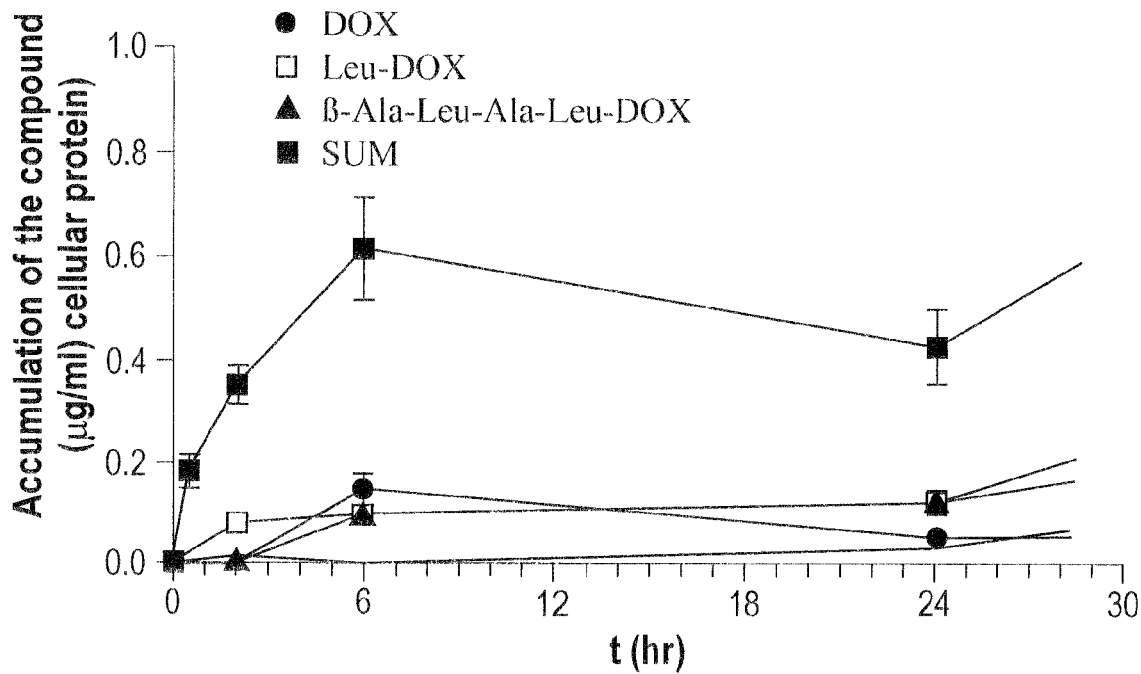
FIG. 28 shows the accumulation of β-Ala-Leu-Ala-Leu-doxorubicin (SEQ ID NO:2) at a concentration of 10 μg/ml by confluent MRC5 fibroblast cells.

L-Leu-DOX accumulates at lower levels, the accumulation reaching 1.4 µg/mg of cellular proteins. The main metabolite is DOX (0.3 µg/mg of cellular proteins) (FIG. 27).

β-Ala-Leu-Ala-Leu-DOX (SEQ ID NO:2) accumulates 112 times less than DOX after 6 hours. Intracellularly, the DOX levels are 1100 times lower after incubation of the cells in the presence of β-Ala-Leu-Ala-Leu-DOX (SEQ ID NO:2) (FIG. 28).

Figure 22:
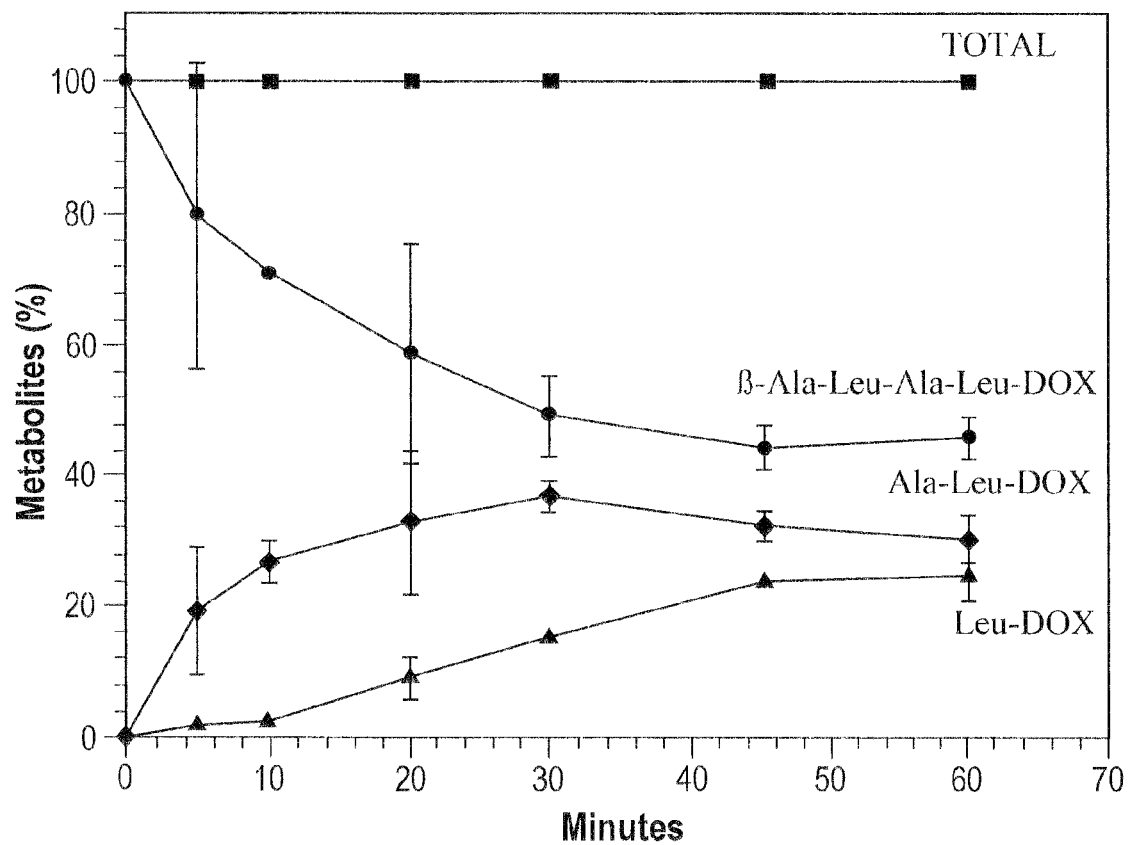
FIG. 22 shows the kinetics of enzymatic hydrolysis of β-Ala-Leu-Ala-Leu-doxorubicin (SEQ ID NO:2) to L-Ala-L-Leu-doxorubicin and L-Leu-doxorubicin in a medium conditioned by MCF7/6 cells.

These results show that, as such, β-Ala-Leu-Ala-Leu-DOX (SEQ ID NO:2) barely enters the cells at all, and that it must be hydrolyzed beforehand in the external medium in the form of Leu-DOX before entering the cells where, intracellularly, the Leu-DOX can thereafter generate DOX (FIG. 22).

These results also show that the intracellular levels of the active therapeutic agent are twice as high in the normal cells as in the tumor cells in the case of DOX. In contrast, in the case of β-Ala-Leu-Ala-Leu-DOX (SEQ ID NO:2) the intracellular levels of DOX are 22 times as high in MCF7 tumor cells compared with MRC5 nontumor cells.

EXAMPLE 13

In Vitro Cytotoxicity with Respect to MCF7/6 Tumor Cells and MRC5 Nontumor Cells The cytotoxicities of β-Ala-Leu-Ala-Leu-DOX (SEQ ID NO:2) of L-Leu-DOX and of DOX were determined on MCF7/6 and MRC5 cells growing in 96-well dishes, incubated in the presence of increasing concentrations of the various compounds. After 72 hours, the cells are incubated for 48 hours in the absence of the anthracycline, and the cytotoxicity is determined by measuring the cellular proteins by Bradford's technique. A series of 9 concentrations are used, ranging from 700 µg/ml to 0.0035 µg/ml, and each measurement represents a mean and standard deviation of 6 values. The experimental points are adjusted to a sigmoid curve which enables the point of inflection, corresponding to the dose at which half of the cells survive (IC50), to be calculated.

The table in Example 12 records the IC50 values, which are, respectively, 0.0025, 0.020 and 3.0 µg/ml; for DOX, L-Leu-DOX and β-Ala-Leu-Ala-Leu-DOX (SEQ ID NO:2) for MCF7/6 human mammary carcinoma cells. For MRC5 human fibroblast line cells, the values are 0.018, 0.30 and 120 µg/ml, respectively.

Figure 29:
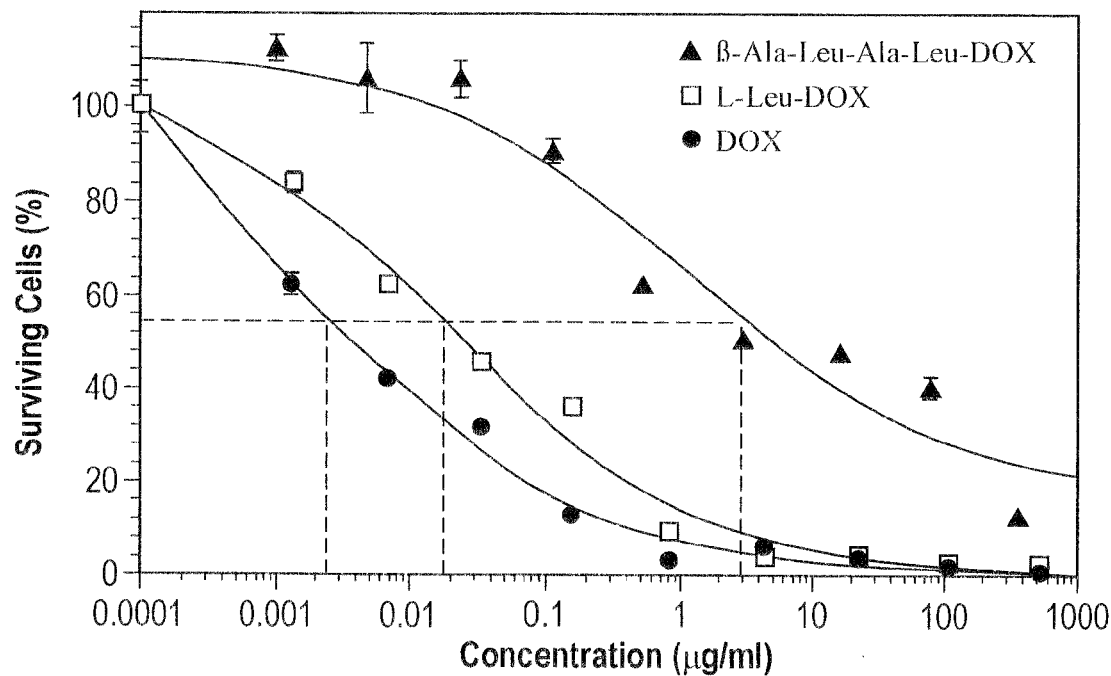
FIG. 29 shows the cytotoxicity of doxorubicin (DOX), of L-Leu-doxorubicin and of β-Ala-Leu-Ala-Leu-doxorubicin (SEQ ID NO:2) with respect to MCF7/6 cells maintained in growth for 72 hours in the presence of said anthracycline derivatives.
Figure 30:
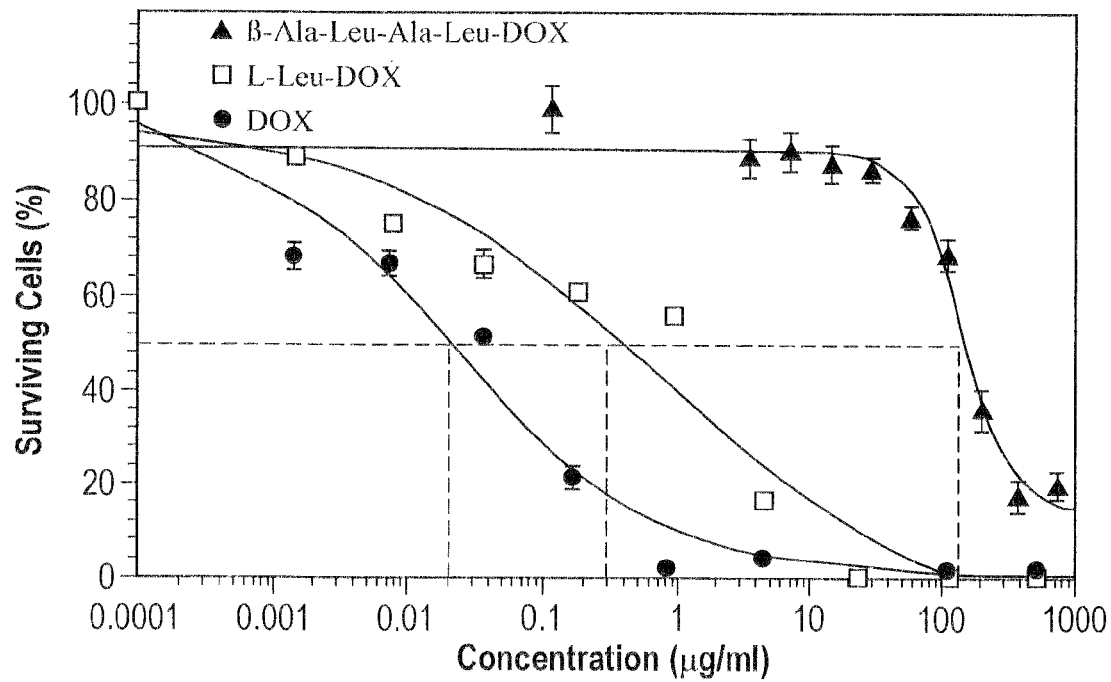
FIG. 30 shows the cytotoxicity of doxorubicin (DOX), of L-Leu-doxorubicin and of β-Ala-Leu-Ala-Leu-doxorubicin (SEQ ID NO:2) with respect to MRC5 fibroblast cells maintained in growth for 72 hours in the presence of said anthracycline derivatives.

These results show that Leu-DOX and β-Ala-Leu-Ala-Leu-DOX (SEQ ID NO:2) are 8 times and 1,000 times, respectively, less cytotoxic than DOX for fibroblast MCF7/6 human mammary carcinoma cells maintained in growth for 72 hours in the presence of the anthracyclines. As regards MRC5 cells, Leu-DOX and β-Ala-Leu-Ala-Leu-DOX (SEQ ID NO:2) are 17 times and 6,700 times, respectively, less cytotoxic than DOX for the cells maintained in growth for 72 hours in the presence of the anthracyclines.

β-Ala-Leu-Ala-Leu-DOX (SEQ ID NO:2) is 40 times as toxic for MCF7 tumor cells as for MRC5 nontumor cells. This is to be set alongside the greater intracellular levels of DOX which were observed in MCF7 cells incubated in the presence of β-Ala-Leu-Ala-Leu-DOX (SEQ ID NO:2) (FIGS. 29 and 30).

The compound is generally characterized by a greater activity against models of solid tumors (for example by injecting tumor cells subcutaneously) than against models of the "leukemic" type obtained after intravenous injection of tumor cells.

Tumor cells injected subcutaneously form a solid tumor at the injection site, and the local concentration of hydrolases secreted by these cells will remain large. When tumor cells are injected intravenously, the hydrolases they secrete will be diluted immediately in the bloodstream.

EXAMPLE 14

In Vivo Acute Toxicity

Figure 31:
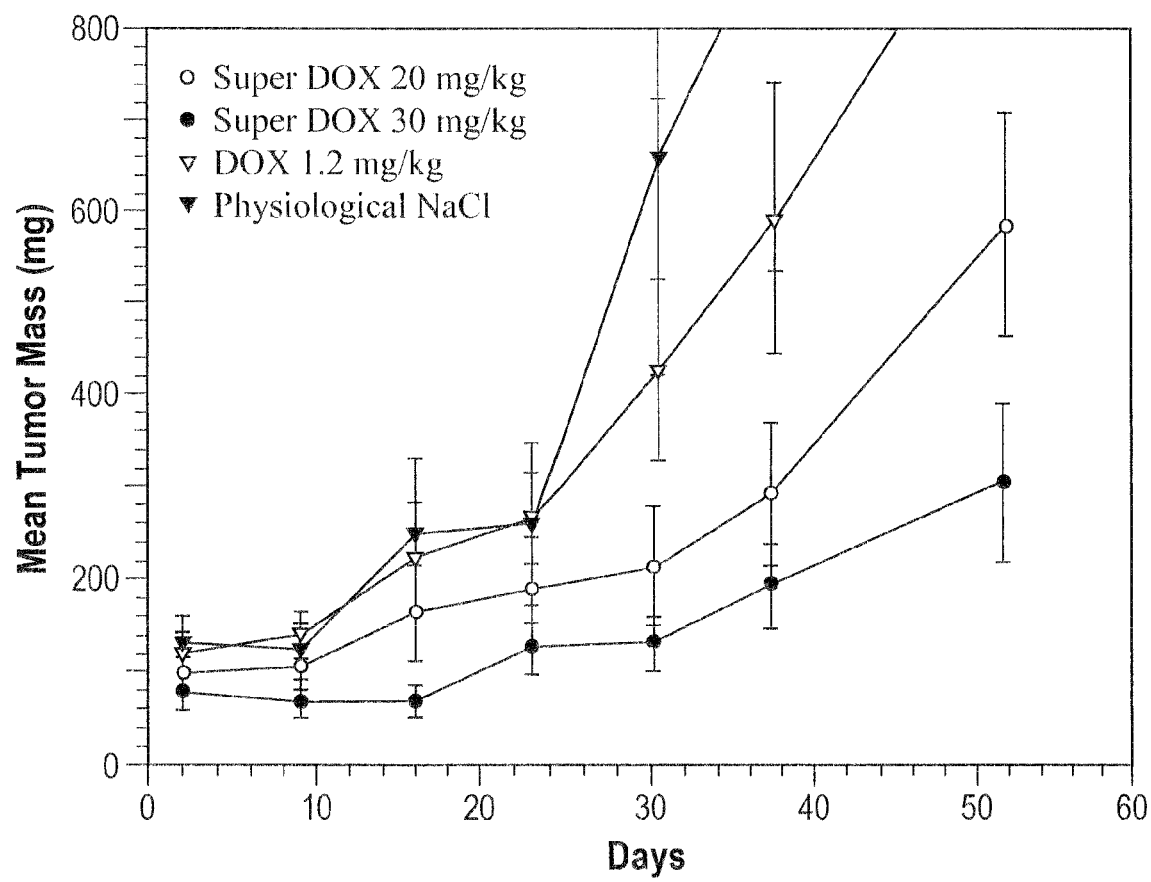
FIG. 31 shows the variation of the mean tumor mass of an MCF7/6 human mammary tumor implanted in athymic mice on day T-21 as a function of the administration of doxorubicin (DOX) and of β-Ala-Leu-Ala-Leu-doxorubicin (SEQ ID NO:2) (super DOX).
Figure 32:
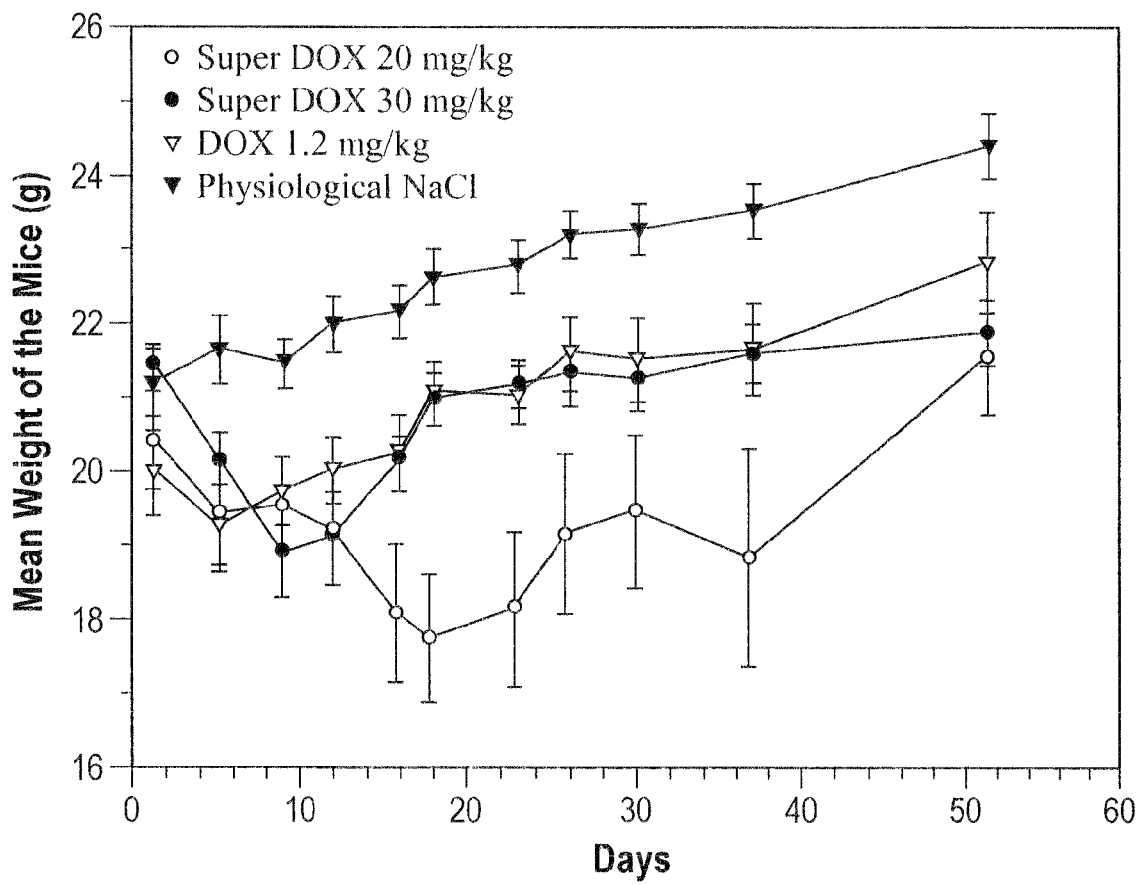
FIG. 32 shows the variation of the mean weight of mice (grams) treated by the administration of doxorubicin (DOX) and of β-Ala-Leu-Ala-Leu-doxorubicin (SEQ ID NO:2) (super DOX).

In addition, the administration of β-Ala-Leu-Ala-Leu-DOX (SEQ ID NO:2) to athymic mice in which an MCF7/6 human mammary tumor has been implanted reduces the progression of the cancerous tumor (FIG. 31) without substantially affecting the mean weight of the mice treated (FIG. 32).

These experiments were carried out according to the protocols described in Example 11.

The Inventors also characterized the protease(s) secreted into the extracellular medium of human mammary carcinoma cells which is/are able to hydrolyze β-Ala-Leu-Ala-Leu-DOX (SEQ ID NO:2). It is confirmed that this/these protease(s) do(es) not correspond to any protease described hitherto.

In effect, the enzyme, provisionally named "COUM", is a metalloprotease which can be inhibited by metal chelators such as EDTA and requires cobalt ion for its activity. Its pH optimum lies between 7.5 and 8.0, ruling out the possibility that it is a cathepsin.

By high performance chromatography and by electrophoresis in the presence of lauryl sulfate, several bands of molecular weight higher than 70 kD are observed.

Figure 33:
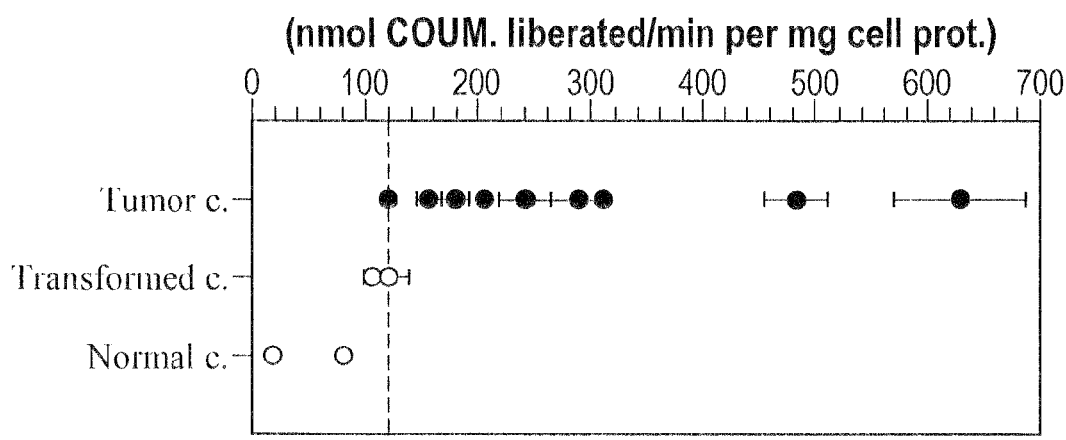
FIG. 33 shows the expression of the free coumarin marker (number of moles of coumarin liberated per milligram of cellular proteins) in test tubes comprising the compound according to the invention with homogenates of tumor cells, homogenates of transformed cells and homogenates of normal cells.

FIG. 33 shows the measurement of the expression of coumarin in test tubes containing the compound according to the invention in homogenates of tumor cells (cancer of the lung, breast, ovaries, etc.), of transformed cells (line of immortalized but noncancerous normal cells) and also of normal cells (fibroblasts and muscle cells).

Hence it is possible, using the compound according to the invention, to diagnose cancerous tumors by the expression of the marker, and thereby to improve the diagnosis of the cancer, the study of the progression of the tumor, the assay of the factors secreted by the tumor cells, etc.

The compound according to the invention may be included in a device for diagnosis and/or for assay comprising different reagents well known to a person skilled in the art.

The diagnostic device of the invention may be used in a method of histological or biochemical diagnosis and/or assay, comprising the taking of tissue, cell or physiological fluid samples from a patient, bringing them into contact with the compound according to the invention under conditions permitting expression of the free marker (optionally involving one or more intermediate reagents) and detecting and/or quantifying the marker liberated.

The invention claimed is:

1. A method for selectively delivering a therapeutic agent to a tumor cell, comprising:
   contacting a tumor activated prodrug, W-Z-M, with the tumor cell; and
   allowing the tumor activated prodrug to be selectively cleaved by a factor secreted by the tumor cell, such that the therapeutic agent is selectively delivered to the tumor cell,
   wherein said tumor activated prodrug, W-Z-M, comprises a component, M, wherein M is a therapeutic agent, said M being linked to a ligand, W-Z, said ligand comprising an arm, Z, linked to a terminal group, W, wherein linkage in the arm, Z, of the ligand, W-Z, or between the arm, Z, and the component, M, prevents intracellular entry of the compound, W-Z-M, wherein said linkage can be selectively cleaved by a factor or factors secreted by a tumor cell so as to permit entry of the therapeutic agent into said tumor cell, and wherein the terminal group, W, includes β-alanyl, and further wherein M is selected from the group consisting of anthracyclines, including doxorubicin and daunorubicin, folic acid derivatives, vinca alkaloids, calicheamycin, mitoxantrone, methotrexate, cytosine arabinosides (ARA-C), adenosine arabinosides (ARA-A), fludarabine phosphate, melphalan, bleomycin, mitomycin, L-canavanine, taxoids, camptothecin and their derivatives, 9-dimethylaminomethyl-10-hydroxycamphtothecin hydrochloride, and their derivatives, optionally linked to a substituted or unsubstituted amino acid.

2. The method of claim 1, wherein the terminal group, W, is β-alanyl.

3. The method of claim 1, wherein the therapeutic agent, M, is doxorubicin or daunorubicin, optionally linked to a substituted or unsubstituted amino acid.

4. The method of claim 1, wherein the arm, Z, is a peptide comprising at least two optionally substituted amino acids.

5. A method for selectively delivering a therapeutic agent to a tumor cell, comprising:
contacting a tumor activated prodrug, W-Z-M, with the tumor cell; and
allowing the tumor activated prodrug to be selectively cleaved by a factor secreted by the tumor cell, such that the therapeutic agent is selectively delivered to the tumor cell,
wherein said tumor activated prodrug, W-Z-M, comprises a component, M, wherein M is a therapeutic agent, said M being linked to a ligand, W-Z, said ligand comprising an arm, Z, linked to a terminal group, W, wherein linkage in the arm, Z, of the ligand, W-Z, or between the arm, Z, and the component, M, prevents intracellular entry of the compound, W-Z-M, wherein said linkage can be selectively cleaved by a factor or factors secreted by a tumor cell so as to permit entry of the therapeutic agent into said tumor cell, wherein the terminal group, W, includes β-alanyl.

6. The method of claim 5, wherein W provides for the stability of the compound when less than 20% of the compound is cleaved during storage of the compound in human blood at 37° C. for 2 hours.

7. The method of claim 5, wherein the terminal group, W, is β-alanyl.

8. The method of claim 5, wherein the therapeutic agent, M, is selected from the group consisting of anthracyclines, including doxorubicin and daunorubicin, folic acid derivatives, vinca alkaloids, calicheamycin, mitoxantrone, methotrexate, cytosine arabinosides (ARA-C) or adenosine arabinosides (ARA-A), fludarabine phosphate, melphalan, bleomycin, mitomycin, L-canavanine, taxoids, camptothecin and their derivatives, 9-dimethylaminomethyl-10-hydroxy-camphtothecin hydrochloride, and their derivatives, optionally linked to a substituted or unsubstituted amino acid.

9. The method of claim 5, wherein the arm, Z, is a peptide comprising at least two optionally substituted amino acids.

10. The method of claim 5, wherein the arm, Z, is a peptide selected from the group consisting of L-leucyl-L-alanyl-L-leucyl, L-leucyl-L-alanyl, L-alanyl-L-leucyl-L-phenylalanyl, and L-alanyl-L-leucyl.

11. The method of claim 5, wherein the tumor activated prodrug is administered to a subject.

12. A method for selectively delivering a therapeutic agent to a tumor cell, comprising:
contacting a tumor activated prodrug, W-Z-M, with the tumor cell; and
allowing the tumor activated prodrug to be selectively cleaved by a factor secreted by the tumor cell, such that the therapeutic agent is selectively delivered to the tumor cell,
wherein said tumor activated prodrug, W-Z-M, comprises a component, M, wherein M is a therapeutic agent, said M being linked to a ligand, W-Z, said ligand comprising an arm, Z, linked to a terminal group, W, wherein linkage in the arm, Z, of the ligand, W-Z, or between the arm, Z, and the component, M, prevents intracellular entry of the compound, W-Z-M, wherein said linkage can be selectively cleaved by a factor or factors secreted by a target cell so as to permit entry of the therapeutic agent into said target cell, wherein the arm, Z, of the ligand, W-Z, is a peptide selected from the group consisting of L-leucyl-L-alanyl-L-leucyl, L-leucyl-L-alanyl, L-alanyl-L-leucyl-L-phenylalanyl, and L-alanyl-L-leucyl, and further wherein the terminal group, W, includes β-alanyl.

13. The method of claim 12, wherein the terminal group, W, is β-alanyl.

14. The method of claim 12, wherein the therapeutic agent, M, is selected from the group consisting of anthracyclines, including doxorubicin and daunorubicin, folic acid derivatives, vinca alkaloids, calicheamycin, mitoxantrone, methotrexate, cytosine arabinosides (ARA-C), adenosine arabinosides (ARA-A), fludarabine phosphate, melphalan, bleomycin, mitomycin, L-canavanine, taxoids, camptothecin and their derivatives, 9-dimethylaminomethyl-10-hydroxy-camphtothecin hydrochloride, and their derivatives, optionally linked to a substituted or unsubstituted amino acid.

* * * * *